(12) United States Patent
Denis et al.

(10) Patent No.: US 9,549,774 B2
(45) Date of Patent: *Jan. 24, 2017

(54) SYSTEM AND METHOD OF CONTROLLING POWER DELIVERY TO A SURGICAL INSTRUMENT

(71) Applicant: Domain Surgical, Inc., Salt Lake City, UT (US)

(72) Inventors: Scott Denis, Murrieta, CA (US); Preston Manwaring, Farmington, UT (US); Phil Eggers, Cottonwood Heights, UT (US); Kim Manwaring, Phoneix, AZ (US)

(73) Assignee: Domain Surgical, Inc., Salt Lake City, UT (US)

( * ) Notice: Subject to any disclaimer, the term of this patent is extended or adjusted under 35 U.S.C. 154(b) by 411 days.

This patent is subject to a terminal disclaimer.

(21) Appl. No.: 14/081,936

(22) Filed: Nov. 15, 2013

(65) Prior Publication Data

US 2014/0074082 A1    Mar. 13, 2014

Related U.S. Application Data

(60) Division of application No. 13/706,481, filed on Dec. 6, 2012, now Pat. No. 8,617,151, and a
(Continued)

(51) Int. Cl.
*A61B 18/08*  (2006.01)
*A61B 18/04*  (2006.01)
(Continued)

(52) U.S. Cl.
CPC ............. *A61B 18/04* (2013.01); *A61B 18/082* (2013.01); *A61B 18/10* (2013.01);
(Continued)

(58) Field of Classification Search
CPC ....... A61B 18/08; A61B 18/082; A61B 18/10; A61B 2018/00994; A61F 7/007–2007/0084
See application file for complete search history.

(56) References Cited

U.S. PATENT DOCUMENTS

| 300,155 A | 6/1884 | Starr |
|---|---|---|
| 770,368 A | 9/1904 | Heath |

(Continued)

FOREIGN PATENT DOCUMENTS

| EP | 0033958 | 8/1981 |
|---|---|---|
| EP | 0 130 671 | 9/1985 |

(Continued)

OTHER PUBLICATIONS

Center for Research in Scientific Computation. *A Domain Wall Theory for Ferroelectric Hysteresis*, Jan. 1999.
(Continued)

*Primary Examiner* — Jaymi Della
(74) *Attorney, Agent, or Firm* — Snow Christensen & Martineau; Sarah W. Matthews; Randall B. Bateman

(57) ABSTRACT

A thermal surgical instrument having a system to control the delivery of power from an energy source to active element located on a tip. The system for controlling delivery to the tip may include a control algorithm which uses one or more measurements, such as tip current, SWR, and rapid changes in reflected power, to manage power without affecting cutting efficacy, and in a manner that may be imperceptible by a surgeon. The system may utilize a state machine to determine the current environment in which the tip may be in. Power delivered to the tip may be selectively managed according to a fixed power index or a repeatedly executed power profile.

18 Claims, 17 Drawing Sheets

Related U.S. Application Data continuation-in-part of application No. 12/647,371, filed on Dec. 24, 2009, now Pat. No. 8,523,852.

(60) Provisional application No. 61/567,603, filed on Dec. 6, 2011, provisional application No. 61/669,671, filed on Jul. 10, 2012, provisional application No. 61/170,203, filed on Apr. 17, 2009, provisional application No. 61/170,220, filed on Apr. 17, 2009, provisional application No. 61/170,207, filed on Apr. 17, 2009.

(51) Int. Cl.
*A61B 18/10* (2006.01)
*A61M 25/00* (2006.01)
*A61B 18/00* (2006.01)
*A61B 18/14* (2006.01)

(52) U.S. Cl.
CPC ...... *A61B 18/1477* (2013.01); *A61B 18/1445* (2013.01); *A61B 2018/00107* (2013.01); *A61B 2018/00577* (2013.01); *A61B 2018/00607* (2013.01); *A61B 2018/00642* (2013.01); *A61B 2018/00791* (2013.01); *A61B 2018/00827* (2013.01); *A61B 2018/00875* (2013.01); *A61B 2018/141* (2013.01); *A61B 2018/1412* (2013.01); *A61M 25/00* (2013.01)

(56) References Cited

U.S. PATENT DOCUMENTS

| | | |
|---|---|---|
| 1,104,053 A | 7/1914 | Lea |
| 1,280,052 A | 9/1918 | Lidberg |
| 1,335,987 A | 4/1920 | Reid |
| 1,366,231 A | 1/1921 | Winter et al. |
| 1,401,104 A | 12/1921 | Kruesheld |
| 1,794,296 A | 2/1931 | Hyams |
| 2,027,854 A | 1/1936 | Breth et al. |
| 2,050,904 A | 8/1936 | Trice |
| 2,120,598 A | 6/1938 | Beuoy |
| 2,250,602 A | 7/1941 | Pierce |
| 2,278,633 A | 4/1942 | Bagnall |
| 2,375,154 A | 5/1945 | Volterra |
| 2,412,977 A | 12/1946 | Eskin |
| 2,501,499 A | 3/1950 | Crowley |
| 2,670,425 A | 12/1954 | Stone |
| 2,735,797 A | 2/1956 | Schjeldahl |
| 2,782,290 A | 2/1957 | Lannan et al. |
| 2,831,242 A | 4/1958 | Kieffer et al. |
| 2,846,560 A | 8/1958 | Jacoby et al. |
| 2,863,036 A | 12/1958 | Mitchell et al. |
| 2,947,345 A | 8/1960 | Schjeldahl |
| 2,960,592 A | 11/1960 | Pierce |
| 3,084,242 A | 4/1963 | Vogler et al. |
| 3,213,259 A | 10/1965 | Bennet et al. |
| 3,350,544 A | 10/1967 | Lennox |
| 3,352,011 A | 11/1967 | Alexander et al. |
| 3,400,252 A | 9/1968 | Hayakawa |
| 3,404,202 A | 10/1968 | Carlson et al. |
| 3,413,442 A | 11/1968 | Buiting et al. |
| 3,414,705 A | 12/1968 | Marcoux |
| 3,434,476 A | 3/1969 | Shaw et al. |
| 3,501,619 A | 3/1970 | Buiting et al. |
| 3,515,837 A | 6/1970 | Ando |
| 3,520,043 A | 7/1970 | Darling |
| 3,556,953 A | 1/1971 | Schulz |
| 3,768,482 A | 10/1973 | Shaw |
| 3,825,004 A | 7/1974 | Durden, III |
| 3,826,263 A | 7/1974 | Cage et al. |
| 3,834,392 A | 9/1974 | Lampman et al. |
| 3,978,312 A | 8/1976 | Barton et al. |
| RE29,088 E | 12/1976 | Shaw |
| 4,089,336 A | 5/1978 | Cage et al. |
| 4,091,813 A | 5/1978 | Shaw et al. |
| RE30,190 E | 1/1980 | Shaw |
| 4,185,632 A | 1/1980 | Shaw |
| 4,196,734 A * | 4/1980 | Harris .............. A61B 18/1206 219/233 |
| 4,198,957 A | 4/1980 | Cage et al. |
| 4,206,759 A | 6/1980 | Shaw |
| 4,207,896 A | 6/1980 | Shaw |
| 4,209,017 A | 6/1980 | Shaw |
| 4,256,945 A | 3/1981 | Carter et al. |
| 4,359,052 A | 11/1982 | Staub |
| 4,364,390 A | 12/1982 | Shaw |
| 4,371,861 A | 2/1983 | Abdelrahman et al. |
| 4,374,517 A | 2/1983 | Hagiwara |
| RE31,723 E | 11/1984 | Shaw |
| 4,481,057 A | 11/1984 | Beard |
| 4,485,810 A | 12/1984 | Beard |
| 4,492,231 A | 1/1985 | Auth |
| 4,493,320 A | 1/1985 | Treat |
| 4,523,084 A | 6/1985 | Tamura et al. |
| 4,549,073 A | 10/1985 | Tamura et al. |
| 4,600,018 A | 7/1986 | James et al. |
| 4,622,966 A | 11/1986 | Beard |
| 4,658,819 A | 4/1987 | Harris et al. |
| 4,658,820 A | 4/1987 | Klicek |
| 4,701,587 A | 10/1987 | Carter et al. |
| 4,752,673 A | 6/1988 | Krumme |
| 4,807,620 A | 2/1989 | Strul et al. |
| 4,839,501 A | 6/1989 | Cowell |
| 4,848,337 A | 7/1989 | Shaw et al. |
| 4,860,745 A | 8/1989 | Farin et al. |
| 4,877,944 A | 10/1989 | Cowell et al. |
| 4,914,267 A | 4/1990 | Derbyshire |
| 4,915,100 A | 4/1990 | Green |
| 4,927,413 A | 5/1990 | Hess |
| 4,938,761 A | 7/1990 | Ensslin |
| 5,003,991 A | 4/1991 | Takayama et al. |
| 5,047,025 A | 9/1991 | Taylor et al. |
| 5,053,595 A | 10/1991 | Derbyshire |
| 5,057,106 A * | 10/1991 | Kasevich .............. A61B 18/18 600/549 |
| 5,071,419 A | 12/1991 | Rydell et al. |
| 5,087,256 A | 2/1992 | Taylor et al. |
| 5,087,804 A | 2/1992 | McGaffigan |
| 5,098,429 A | 3/1992 | Sterzer |
| 5,107,095 A | 4/1992 | Derbyshire |
| 5,182,427 A | 1/1993 | McGaffigan |
| 5,189,271 A | 2/1993 | Derbyshire |
| 5,197,649 A | 3/1993 | Bessler et al. |
| 5,203,782 A | 4/1993 | Gudov et al. |
| 5,209,725 A | 5/1993 | Roth |
| 5,211,646 A | 5/1993 | Alperovich et al. |
| 5,217,460 A | 6/1993 | Knoepfler |
| 5,300,068 A | 4/1994 | Rosar et al. |
| 5,300,750 A | 4/1994 | Carter, Jr. et al. |
| 5,308,311 A | 5/1994 | Eggers et al. |
| 5,318,564 A | 6/1994 | Eggers |
| 5,364,392 A | 11/1994 | Warner et al. |
| 5,370,645 A | 12/1994 | Klicek et al. |
| 5,370,675 A | 12/1994 | Edwards et al. |
| 5,376,094 A | 12/1994 | Kline |
| 5,382,247 A | 1/1995 | Cimino et al. |
| 5,400,267 A | 3/1995 | Denen et al. |
| 5,411,508 A | 5/1995 | Bessler et al. |
| 5,423,808 A | 6/1995 | Edwards et al. |
| 5,425,731 A * | 6/1995 | Daniel ................ A61B 18/082 219/229 |
| 5,445,635 A * | 8/1995 | Denen .................... A61B 18/08 219/240 |
| 5,472,443 A | 12/1995 | Cordis et al. |
| 5,475,203 A | 12/1995 | McGaffigan |
| 5,480,397 A | 1/1996 | Eggers |
| 5,480,398 A | 1/1996 | Eggers |
| 5,496,312 A | 3/1996 | Klicek |
| 5,496,314 A | 3/1996 | Eggers |
| 5,507,743 A | 4/1996 | Edwards et al. |
| 5,540,679 A | 7/1996 | Fram et al. |
| 5,540,681 A | 7/1996 | Strul et al. |
| 5,542,916 A | 8/1996 | Hirsch et al. |

(56) References Cited

U.S. PATENT DOCUMENTS

| | | |
|---|---|---|
| 5,571,153 A | 11/1996 | Wallsten |
| 5,573,533 A | 11/1996 | Strul |
| 5,593,406 A | 1/1997 | Eggers et al. |
| 5,595,565 A | 1/1997 | Treat et al. |
| 5,611,798 A | 3/1997 | Eggers |
| 5,628,771 A | 5/1997 | Mizukawa et al. |
| 5,674,219 A | 10/1997 | Monson et al. |
| 5,707,369 A | 1/1998 | Vaitekunas et al. |
| 5,707,402 A | 1/1998 | Heim |
| 5,807,392 A | 9/1998 | Eggers |
| 5,807,393 A | 9/1998 | Williamson, IV et al. |
| 5,827,269 A | 10/1998 | Saadat |
| 5,836,874 A | 11/1998 | Swanson et al. |
| 5,836,943 A | 11/1998 | Miller, III |
| 5,843,019 A | 12/1998 | Eggers et al. |
| 5,911,719 A | 6/1999 | Eggers |
| 5,964,759 A | 10/1999 | Yamanashi et al. |
| 6,004,316 A | 12/1999 | Laufer |
| 6,006,755 A | 12/1999 | Edwards |
| 6,015,415 A | 1/2000 | Avellanet |
| 6,035,238 A | 3/2000 | Ingle et al. |
| 6,038,017 A | 3/2000 | Pinsukanjana et al. |
| 6,039,733 A | 3/2000 | Buysse et al. |
| 6,066,138 A | 5/2000 | Sheffer et al. |
| 6,161,048 A | 12/2000 | Sluijter et al. |
| 6,190,382 B1 | 2/2001 | Ormsby et al. |
| 6,210,403 B1 | 4/2001 | Klicek |
| 6,228,084 B1 | 5/2001 | Kirwan, Jr. |
| 6,241,723 B1 | 6/2001 | Heim et al. |
| 6,287,305 B1 | 9/2001 | Heim et al. |
| 6,290,697 B1 | 9/2001 | Tu et al. |
| 6,350,262 B1 | 2/2002 | Ashley |
| 6,358,273 B1 | 3/2002 | Strul et al. |
| 6,454,781 B1 | 9/2002 | Witt et al. |
| 6,533,781 B2 | 3/2003 | Heim et al. |
| 6,602,252 B2 | 8/2003 | Mollenauer |
| 6,604,003 B2 | 8/2003 | Fredricks et al. |
| 6,626,901 B1 | 9/2003 | Treat et al. |
| 6,632,182 B1 | 10/2003 | Treat |
| 6,692,489 B1 | 2/2004 | Heim et al. |
| 6,726,683 B1 | 4/2004 | Shaw |
| 6,821,273 B2 | 11/2004 | Mollenauer |
| 6,860,880 B2 | 3/2005 | Treat et al. |
| 6,908,463 B2 | 6/2005 | Treat et al. |
| 6,911,026 B1 | 6/2005 | Hall et al. |
| 6,912,911 B2 | 7/2005 | Oh et al. |
| 6,980,862 B2 | 12/2005 | Fredricks et al. |
| 6,980,865 B1 | 12/2005 | Wang et al. |
| 7,011,656 B2 | 3/2006 | McGaffigan |
| 7,025,065 B2 | 4/2006 | McGaffigan et al. |
| 7,083,613 B2 | 8/2006 | Treat |
| 7,112,201 B2 | 9/2006 | Truckai et al. |
| 7,122,030 B2 | 10/2006 | Flores et al. |
| 7,164,968 B2 | 1/2007 | Treat et al. |
| 7,175,621 B2 | 2/2007 | Heim et al. |
| 7,211,079 B2 | 5/2007 | Treat |
| 7,211,080 B2 | 5/2007 | Treat et al. |
| 7,235,073 B2 | 6/2007 | Levine et al. |
| 7,300,452 B2 | 11/2007 | Gleich |
| 7,317,275 B2 | 1/2008 | Treat |
| 7,326,202 B2 | 2/2008 | McGaffigan |
| 7,329,255 B2 | 2/2008 | McGaffigan |
| 7,377,919 B2 | 5/2008 | Heim et al. |
| 7,396,356 B2 | 7/2008 | Mollenauer |
| 7,435,249 B2 | 10/2008 | Buysse et al. |
| 7,473,250 B2 | 1/2009 | Makin et al. |
| 7,473,253 B2 | 1/2009 | Dycus et al. |
| 7,494,492 B2 | 2/2009 | Da Silva et al. |
| 7,528,663 B2 | 5/2009 | Naletov et al. |
| 7,533,719 B2 | 5/2009 | Hinson |
| 7,540,324 B2 | 6/2009 | de Rouffignac |
| 7,549,470 B2 | 6/2009 | Vinegar |
| 7,553,309 B2 | 6/2009 | Buysse et al. |
| 7,556,095 B2 | 7/2009 | Vinegar |
| 7,556,096 B2 | 7/2009 | Vinegar |
| 7,559,367 B2 | 7/2009 | Vinegar |
| 7,559,368 B2 | 7/2009 | Vinegar |
| 7,562,706 B2 | 7/2009 | Li et al. |
| 7,562,707 B2 | 7/2009 | Miller |
| 7,578,815 B2 | 8/2009 | Howell |
| 7,581,589 B2 | 9/2009 | Roes et al. |
| 7,584,789 B2 | 9/2009 | Mo et al. |
| 7,588,565 B2 | 9/2009 | Marchitto et al. |
| 7,588,566 B2 | 9/2009 | Treat et al. |
| 7,591,310 B2 | 9/2009 | Minderhoud |
| 7,597,147 B2 | 10/2009 | Vitek |
| 7,604,052 B2 | 10/2009 | Roes |
| 7,610,962 B2 | 11/2009 | Fowler |
| 7,613,523 B2 | 11/2009 | Eggers et al. |
| 7,631,689 B2 | 12/2009 | Vinegar |
| 7,631,690 B2 | 12/2009 | Vinegar |
| 7,632,295 B2 | 12/2009 | Flores |
| 7,635,023 B2 | 12/2009 | Goldberg |
| 7,635,024 B2 | 12/2009 | Karanikas |
| 7,635,025 B2 | 12/2009 | Vinegar |
| 7,678,105 B2 | 3/2010 | McGreevy et al. |
| 7,686,804 B2 | 3/2010 | Johnson et al. |
| 7,699,842 B2 | 4/2010 | Buysse et al. |
| 7,702,397 B2 | 4/2010 | Fredricks et al. |
| 7,776,035 B2 | 8/2010 | Rick et al. |
| 7,828,798 B2 | 11/2010 | Buysse et al. |
| 7,871,406 B2 | 1/2011 | Nields et al. |
| 7,879,033 B2 | 2/2011 | Sartor et al. |
| 7,887,535 B2 | 2/2011 | Lands et al. |
| 7,922,713 B2 | 4/2011 | Geisel |
| 7,931,649 B2 | 4/2011 | Couture et al. |
| 7,938,779 B2 | 5/2011 | Sakurai et al. |
| 7,951,149 B2 | 5/2011 | Carlton |
| 7,951,150 B2 | 5/2011 | Johnson et al. |
| 7,959,633 B2 | 6/2011 | Sartor et al. |
| 7,963,965 B2 | 6/2011 | Buysse et al. |
| 7,972,334 B2 | 7/2011 | McGreevy et al. |
| 7,972,335 B2 | 7/2011 | McGreevy et al. |
| 7,981,113 B2 | 7/2011 | Truckai et al. |
| 8,062,290 B2 | 11/2011 | Buysse et al. |
| 8,100,896 B2 | 1/2012 | Rodhajsky |
| 8,100,908 B2 | 1/2012 | McGaffigan et al. |
| 8,104,956 B2 | 1/2012 | Blaha |
| 8,105,323 B2 | 1/2012 | Buysse et al. |
| 8,211,105 B2 | 7/2012 | Buysse et al. |
| 8,241,284 B2 | 8/2012 | Dycus et al. |
| 8,287,528 B2 | 10/2012 | Wham et al. |
| 8,377,052 B2 | 2/2013 | Manwaring et al. |
| 8,377,057 B2 | 2/2013 | Rick et al. |
| 8,398,626 B2 | 3/2013 | Buysse et al. |
| 8,480,666 B2 | 7/2013 | Buysse et al. |
| 8,568,402 B2 | 10/2013 | Buysse et al. |
| 8,591,506 B2 | 11/2013 | Wham et al. |
| 8,667,674 B2 | 3/2014 | Buysse |
| 8,672,938 B2 | 3/2014 | Buysse et al. |
| 2001/0014804 A1 | 8/2001 | Goble et al. |
| 2002/0019627 A1 | 2/2002 | Maguire et al. |
| 2002/0019644 A1 | 2/2002 | Hastings et al. |
| 2002/0026188 A1 | 2/2002 | Balbierz et al. |
| 2002/0029037 A1 | 3/2002 | Kim |
| 2002/0029062 A1 | 3/2002 | Satake |
| 2002/0068931 A1 | 6/2002 | Wong et al. |
| 2002/0087156 A1 | 7/2002 | Maguire et al. |
| 2002/0120261 A1 | 8/2002 | Balbierz et al. |
| 2002/0133148 A1 | 9/2002 | Daniel et al. |
| 2002/0165529 A1* | 11/2002 | Danek .................. A61B 18/14 606/28 |
| 2002/0173787 A1 | 11/2002 | Buysse et al. |
| 2003/0004507 A1 | 1/2003 | Francischelli et al. |
| 2003/0055417 A1 | 3/2003 | Truckai et al. |
| 2003/0055424 A1 | 3/2003 | Ciarrocca |
| 2003/0060818 A1 | 3/2003 | Kannenberg et al. |
| 2003/0073987 A1 | 4/2003 | Sakurai et al. |
| 2003/0073989 A1 | 4/2003 | Hoey et al. |
| 2003/0109871 A1 | 6/2003 | Johnson et al. |
| 2003/0139741 A1* | 7/2003 | Goble ................ A61B 18/1445 606/48 |
| 2003/0144660 A1 | 7/2003 | Mollenauer |
| 2003/0171747 A1 | 9/2003 | Kanehira et al. |

(56) References Cited

U.S. PATENT DOCUMENTS

| | | |
|---|---|---|
| 2003/0176873 A1 | 9/2003 | Chernenko et al. |
| 2003/0195499 A1 | 10/2003 | Prakash et al. |
| 2003/0199755 A1 | 10/2003 | Halperin |
| 2004/0006335 A1 | 1/2004 | Garrison |
| 2004/0030330 A1 | 2/2004 | Brassell et al. |
| 2004/0034349 A1 | 2/2004 | Kirwan, Jr. et al. |
| 2004/0049185 A1 | 3/2004 | Latterell et al. |
| 2004/0059345 A1 | 3/2004 | Nakao et al. |
| 2004/0073256 A1 | 4/2004 | Marchitto |
| 2004/0167506 A1 | 8/2004 | Chen |
| 2004/0176756 A1 | 9/2004 | McGaffigan |
| 2004/0187875 A1 | 9/2004 | He et al. |
| 2004/0243120 A1 | 12/2004 | Orszulak et al. |
| 2005/0021016 A1 | 1/2005 | Malecki et al. |
| 2005/0033338 A1 | 2/2005 | Ferree |
| 2005/0072827 A1 | 4/2005 | Mollenauer |
| 2005/0107776 A1 | 5/2005 | Mcgaffigan et al. |
| 2005/0113824 A1 | 5/2005 | Sartor et al. |
| 2005/0197661 A1 | 9/2005 | Carrison et al. |
| 2005/0245919 A1 | 11/2005 | Van der Welde |
| 2005/0273111 A1 | 12/2005 | Ferree et al. |
| 2005/0283067 A1 | 12/2005 | Sobe |
| 2005/0283149 A1 | 12/2005 | Thorne et al. |
| 2005/0288659 A1 | 12/2005 | Kimura et al. |
| 2006/0142824 A1 | 6/2006 | Zikorus et al. |
| 2006/0161149 A1 | 7/2006 | Privitera et al. |
| 2006/0167450 A1 | 7/2006 | Johnson et al. |
| 2006/0212030 A1 | 9/2006 | McGaffigan |
| 2006/0212031 A1 | 9/2006 | McGaffigan et al. |
| 2006/0217700 A1 | 9/2006 | Garito et al. |
| 2006/0217706 A1 | 9/2006 | Lau et al. |
| 2006/0241587 A1 | 10/2006 | Heim et al. |
| 2006/0241588 A1 | 10/2006 | Heim et al. |
| 2006/0241589 A1 | 10/2006 | Heim et al. |
| 2006/0271037 A1 | 11/2006 | Maroney et al. |
| 2007/0005054 A1 | 1/2007 | Heim et al. |
| 2007/0005055 A1 | 1/2007 | Heim et al. |
| 2007/0005056 A1 | 1/2007 | Heim et al. |
| 2007/0005057 A1 | 1/2007 | Heim et al. |
| 2007/0005058 A1 | 1/2007 | Heim et al. |
| 2007/0005059 A1 | 1/2007 | Heim et al. |
| 2007/0005060 A1 | 1/2007 | Heim et al. |
| 2007/0016181 A1 | 1/2007 | van der Weide et al. |
| 2007/0016272 A1* | 1/2007 | Thompson ............. A61B 18/08 607/96 |
| 2007/0060920 A1 | 3/2007 | Weitzner |
| 2007/0073282 A1 | 3/2007 | McGaffigan et al. |
| 2007/0100336 A1 | 5/2007 | McFarlin et al. |
| 2007/0100405 A1* | 5/2007 | Thompson ............. A61B 18/08 607/113 |
| 2007/0106294 A1 | 5/2007 | Nesbitt |
| 2007/0127897 A1 | 6/2007 | John et al. |
| 2007/0131428 A1 | 6/2007 | Willem Cornelis den Boestert et al. |
| 2007/0173811 A1 | 7/2007 | Couture et al. |
| 2007/0208339 A1 | 9/2007 | Arts et al. |
| 2007/0239151 A1 | 10/2007 | Atalar et al. |
| 2007/0270924 A1 | 11/2007 | McCann et al. |
| 2008/0017380 A1 | 1/2008 | Vinegar |
| 2008/0033419 A1 | 2/2008 | Nields et al. |
| 2008/0035346 A1 | 2/2008 | Nair et al. |
| 2008/0035347 A1 | 2/2008 | Brady |
| 2008/0035705 A1 | 2/2008 | Menotti |
| 2008/0038144 A1 | 2/2008 | Maziasz |
| 2008/0057129 A1 | 3/2008 | Van Wyk et al. |
| 2008/0119841 A1 | 5/2008 | Geisel |
| 2008/0128134 A1 | 6/2008 | Mudunuri et al. |
| 2008/0135253 A1 | 6/2008 | Vinegar |
| 2008/0135254 A1 | 6/2008 | Vinegar |
| 2008/0142216 A1 | 6/2008 | Vinegar |
| 2008/0142217 A1 | 6/2008 | Pieterson et al. |
| 2008/0161800 A1 | 7/2008 | Wang et al. |
| 2008/0173444 A1 | 7/2008 | Stone et al. |
| 2008/0174115 A1 | 7/2008 | Lambirth |
| 2008/0185147 A1 | 8/2008 | Vinegar |
| 2008/0187989 A1 | 8/2008 | McGreevy et al. |
| 2008/0217003 A1 | 9/2008 | Kuhlman |
| 2008/0217016 A1 | 9/2008 | Stegemeier |
| 2008/0228135 A1 | 9/2008 | Snoderly |
| 2008/0236831 A1 | 10/2008 | Hsu |
| 2008/0255642 A1* | 10/2008 | Zarins ............... A61B 18/1206 607/99 |
| 2008/0277113 A1 | 11/2008 | Stegemeier |
| 2008/0281310 A1 | 11/2008 | Dunning et al. |
| 2008/0281315 A1 | 11/2008 | Gines |
| 2008/0319438 A1 | 12/2008 | DeCarlo |
| 2009/0014180 A1 | 1/2009 | Stegemeier |
| 2009/0014181 A1 | 1/2009 | Vinegar |
| 2009/0093811 A1 | 4/2009 | Koblish et al. |
| 2009/0112200 A1 | 4/2009 | Eggers |
| 2009/0118729 A1 | 5/2009 | Auth et al. |
| 2009/0118730 A1 | 5/2009 | Mollenauer |
| 2009/0198224 A1 | 8/2009 | McGaffigan |
| 2009/0248002 A1 | 10/2009 | Takashino et al. |
| 2009/0292347 A1 | 11/2009 | Asmus et al. |
| 2009/0306644 A1 | 12/2009 | Mayse et al. |
| 2009/0312753 A1 | 12/2009 | Shadduck |
| 2010/0004650 A1 | 1/2010 | Ormsby et al. |
| 2010/0082022 A1 | 4/2010 | Haley et al. |
| 2010/0152725 A1 | 6/2010 | Pearson et al. |
| 2010/0198216 A1 | 8/2010 | Palanker |
| 2010/0268205 A1 | 10/2010 | Manwaring et al. |
| 2010/0268206 A1 | 10/2010 | Manwaring et al. |
| 2010/0268207 A1 | 10/2010 | Manwaring et al. |
| 2010/0268208 A1 | 10/2010 | Manwaring et al. |
| 2010/0268209 A1 | 10/2010 | Manwaring et al. |
| 2010/0268210 A1 | 10/2010 | Manwaring et al. |
| 2010/0268211 A1 | 10/2010 | Manwaring et al. |
| 2010/0268212 A1 | 10/2010 | Manwaring et al. |
| 2010/0268213 A1 | 10/2010 | Manwaring et al. |
| 2010/0268214 A1 | 10/2010 | Manwaring et al. |
| 2010/0268215 A1 | 10/2010 | Manwaring et al. |
| 2010/0268216 A1 | 10/2010 | Manwaring et al. |
| 2010/0268218 A1 | 10/2010 | Ormsby et al. |
| 2011/0004204 A1 | 1/2011 | Dodde et al. |
| 2011/0054456 A1 | 3/2011 | Thompson et al. |
| 2011/0092971 A1 | 4/2011 | Sartor et al. |
| 2011/0152857 A1 | 6/2011 | Ingle |
| 2012/0059367 A1 | 3/2012 | Buysse et al. |
| 2012/0071712 A1 | 3/2012 | Manwaring et al. |
| 2012/0130256 A1 | 5/2012 | Buysse et al. |
| 2012/0150170 A1 | 6/2012 | Buysse et al. |
| 2012/0226270 A1 | 9/2012 | Manwaring et al. |
| 2012/0259323 A1 | 10/2012 | Manwaring et al. |
| 2012/0296326 A1 | 11/2012 | Manwaring et al. |
| 2012/0303026 A1 | 11/2012 | Dycus et al. |
| 2012/0330295 A1 | 12/2012 | Manwaring et al. |
| 2013/0006240 A1 | 1/2013 | McNally et al. |
| 2013/0012934 A1 | 1/2013 | Manwaring et al. |
| 2013/0023866 A1 | 1/2013 | Stringham et al. |
| 2013/0041367 A1 | 2/2013 | Wham et al. |
| 2014/0058381 A1 | 2/2014 | Wham et al. |
| 2014/0058384 A1 | 2/2014 | Buysse et al. |
| 2014/0058385 A1 | 2/2014 | Wham et al. |
| 2014/0100559 A1 | 4/2014 | Wham et al. |
| 2014/0180266 A1 | 6/2014 | Buysse et al. |

FOREIGN PATENT DOCUMENTS

| | | |
|---|---|---|
| EP | 2036512 A1 | 3/2009 |
| EP | 2070486 | 6/2009 |
| GB | 2 022 974 | 12/1978 |
| GB | 1 546 624 | 5/1979 |
| JP | 03051179 | 8/1996 |
| JP | 2558584 | 9/1996 |
| RU | 2 072 118 | 1/1997 |
| WO | WO-82/00746 | 3/1982 |
| WO | WO 92/17121 | 10/1992 |
| WO | WO-93/21839 | 11/1993 |
| WO | WO-96/26677 | 11/1996 |
| WO | WO 9937227 A1 | 7/1999 |
| WO | WO-01/06943 | 2/2001 |
| WO | WO-2004/014217 | 2/2004 |
| WO | WO-2004/076146 | 9/2004 |

(56) References Cited

FOREIGN PATENT DOCUMENTS

| WO | WO-2006/017517 | 2/2006 |
|---|---|---|
| WO | WO-2006/029649 | 3/2006 |
| WO | WO 2007080578 A2 | 7/2007 |
| WO | WO-2008/060668 | 5/2008 |

OTHER PUBLICATIONS

Metcal Soldering Iron Catalog—2006.
URSI EMTS 2004, pp. 489-491, *Electromagnetic Probes for Living Tissue Cauterization*.
"High Temp Metals." NI2001201 Technical Data. High Temp Metals, Inc., n.d. Web Jul. 13, 2012. <http://www.hightempmetals.com/techdatafnitempNi200data.php.
International Preliminary Report on Patentability from related PCT Patent Application No. PCT/US2010/031114, Nov. 1, 2011.
International Preliminary Report on Patentability from related PCT Patent Application No. PCT/US2010/031114, Jan. 21, 2011.
International Preliminary Report on Patentability from related PCT Patent Application No. PCT/US2011/050417, Apr. 12, 2012.
International Preliminary Report on Patentability from related PCT Patent Application No. PCT/US2012/032656, Oct. 23, 2012.
International Preliminary Report on Patentability from related PCT Patent Application No. PCT/US2012/032659, Nov. 23, 2012.
International Preliminary Report on Patentability from related PCT Patent Application No. PCT/US2012/038005, Nov. 23, 2012.
International Preliminary Report on Patentability from related PCT Patent Application No. PCT/US2012/055229, Feb. 1, 2013.
Written Opinion of the International Preliminary Examining Authority from related PCT Patent Application No. PCT/US2011/050417, Feb. 6, 2013.
International Preliminary Report on Patentability from related PCT Patent Application No. PCT/US2012/068027, Feb. 25, 2013.
Visioli, Antonio. Practice PID Control: London: Springer-Verlag, 2006. 1-18. Print.
International Search Report and Written Opinion from related PCT Application US2012/032661, Aug. 19, 2013.
International Search Report and Written Opinion from related PCT Application US2012/032659, Oct. 8, 2013.
International Search Report and Written Opinion from related PCT Application US2012/032565, Oct. 8, 2013.
International Preliminary Report on Patentability from related PCT Application US2012/038005, Nov. 19, 2013.
Translation of Office Action from related Japanese Patent Application No. 2012-506188, PCT US2010-031114.
International Preliminary Report on Patentability from PCT/US2012/068027, dated Jun. 10, 2014.
European Search Report from European Application No. 12865504.0-1652, dated Nov. 28, 2014.

* cited by examiner

SYSTEM AND METHOD OF CONTROLLING POWER DELIVERY TO A SURGICAL INSTRUMENT

THE FIELD OF THE INVENTION

The present application is a division of patent application Ser. No. 13/706,481, filed Dec. 6, 2012, now U.S. Pat. No. 8,617,151; which claims priority to provisional application Nos. 61/669,671, filed Jul. 10, 2012 and 61/567,603, filed Dec. 6, 2011. Application Ser. No. 13/706,481 is a continuation-in-part of application Ser. No. 12/647,371, filed Dec. 24, 2009, now U.S. Pat. No. 8,523,852; which claims priority to provisional application Nos. 61/170,207, 61/170,203, and 61/170,220, all filed Apr. 17, 2009.

The present invention relates to electrosurgical and/or thermal surgical instruments. More specifically, the present invention relates to a system and method of controlling the delivery of power from an energy source to the instrument.

BACKGROUND

It is becoming more common to use electrosurgical and/or thermal devices during surgery because such devices may provide benefits over traditional medical devices. For example, electrosurgical and/or thermal devices may allow a surgeon to make precise incisions with limited blood loss. Because of their advantages, electrosurgical and/or thermal devices may be used in dermatological, gynecological, cardiac, plastic, ocular, spine, ENT, maxillofacial, orthopedic, urological, neurological and general surgical procedures as well as certain dental procedures, just to name a few.

Surgery generally involves cutting, repairing and/or removing tissue or other materials. Electrosurgical and/or thermal instruments may be used to perform each of these procedures by using the electrosurgical and/or thermal instrument to heat the tissue or other material to a desired temperature. Tissue may react differently, however, at different temperatures. If the temperature of the electrosurgical and/or thermal instrument is not properly controlled, then undesired results may occur which may lead to an adverse outcome for the patient.

Furthermore, a surgeon may be required to use an electrosurgical and/or thermal instrument for a prolonged period of time during a given procedure. During this time the instrument may be intermittently moved in and out of contact with a portion of the patient's body. This can lead to problems both with heat management within the device itself as well as heat management of the heated surgical tip of the instrument. When the instrument is not in contact with a portion of the patient's tissue, body fluid, etc., it is held in the air above the patient's body, and it may be important to limit the power delivered to the instrument to minimize transfer of heat to areas of the instrument where heat is unwanted or even detrimental. For example, if heat transfer to a portion of the electrosurgical and/or thermal instrument which is gripped by the surgeon is not properly controlled, the device may become too hot and the surgeon may not be able to handle the instrument for the time necessary to complete the procedure.

Additionally, if the active portion of the electrosurgical and/or thermal instrument, such as a thermal element, is overheated or exposed to excessive thermal stress, the thermal element may be damaged.

Thus there is a need for improved system and method of controlling the delivery of power from an energy source to an electrosurgical and/or thermal surgical instrument to prevent overheating of the instrument and/or the heated surgical tip.

SUMMARY OF THE INVENTION

It is an object of the present invention to provide an improved electrosurgical and/or thermal surgical instrument.

According to one aspect of the invention, the instrument may include software and hardware to manage power delivery from an energy source to the instrument.

According to another aspect of the invention, controlling power delivery to the electrosurgical instrument may include using an algorithm which varies the power delivery to an active element of the instrument, thus varying the operational characteristics of the instrument according to the environment of the active element (e.g. whether the active element is being used for tissue treatment or being held in the air). The algorithm may be managed at a fixed power index between about 5 W and 125 W and may be used to deliver a desired power to the electrosurgical and/or thermal surgical instrument in a consistent manner, prevent the active element of the instrument from exceeding the Curie point, and/or prevent overheating of the instrument when the active element is in the air. The control algorithm may allow a surgeon to use the optimal temperature for a desired tissue effect, and also allow the surgeon to select surgical tips having different configurations while providing the desired control when using these different surgical tips.

According to another aspect of the invention, controlling power delivery to the electrosurgical instrument may include using a single or cascaded proportional-integral-derivative controller ("PID") for forward power or net power, PID tip current limiting control, standing wave ratio ("SWR") threshold limiting, and/or Load/Air detection.

According to another aspect of the invention, the thermal surgical instrument may include a handpiece responsible for current sensing, temperature sensing, impedance sensing, etc.

According to another aspect of the invention, current data, temperature data, impedance data, etc. which is sensed by the handpiece, or other parts of the thermal surgical instrument, may be sent to a control console which includes a microcontroller, microprocessor, or the like.

According to another aspect of the invention, current data, temperature data, impedance data, etc. may be sent to a control console on a substantially continuous basis. For example, the data may be sent to the control console at intervals of about 10 milliseconds.

According to another aspect of the invention, the surgical instrument may include a thermal element. The thermal element may include, for example, a conductor having a ferromagnetic material plated thereon, a solid ferromagnetic heating element, a ferromagnetic sleeve disposed on an insulated conductor such that heating of the ferromagnetic sleeve is substantially purely inductive, etc.

According to another aspect of the invention, the thermal element of the thermal surgical instrument may be removably received by a handpiece so that various thermal elements may be used with the handpiece.

According to another aspect of the invention, a surgical instrument may include information necessary to manage the power output of the thermal element, which may differ according to the shape, dimension, or configuration of the thermal element (e.g., blade, loop, snare, forceps, shears, minimally invasive surgery instruments, probes, catheters etc.). For example, the information may be stored in a single storage device (such as an EEPROM, flash device, lasered ROM or fram, etc.) located in the handpiece, or multiple storage devices located at various locations on a surgical instrument system of the present invention.

According to another aspect of the invention, a surgical instrument may include the following information necessary to manage the power output of the thermal element, such as: current limit; allowable power settings; SWR limit by power level; serial number; calibration constants; tip identification; timing constants (e.g. cool down); etc.

According to another aspect of the invention, the thermal surgical instrument system may include software. The software may use information received from the thermal surgical instrument to implement a variable stage state machine. For example, the software may receive information from a handpiece, tip, and/or power meter of the thermal surgical instrument to implement a 5-stage state machine. The stages of the state machine may include RF On (e.g. RF power has just been enabled), Air (the thermal element of the surgical instrument is in air), Pre-Load (the thermal element is suspected to be in tissue), Transition (the thermal element is suspected to be transitioning from tissue to air), and Load (the tip is confirmed to be in tissue).

According to still another aspect of the invention, controlling power delivery to the thermal surgical instrument may include a power profile control algorithm which includes a group of start/end duration segments to intermittently increase the power delivered to the tip of an electrosurgical instrument. Thus, when it is desired to use the instrument to treat tissue with a tip operated at lower temperatures, for example when coagulating tissue, the power control algorithm may intermittently increase the power delivered to the tip so as to substantially prevent to tip from sticking to the tissue being treated.

According to yet another aspect of the invention, a thermal surgical instrument of the present invention may have one or more controls for selectively managing power delivery to a surgical tip according to a fixed power index or a repeatedly executed power profile.

These and other aspects of the present invention are realized in a thermally adjustable surgical instrument as shown and described in the following figures and related description.

BRIEF DESCRIPTION OF THE DRAWINGS

Various embodiments of the present invention are shown and described in reference to the numbered drawings wherein.

It will be appreciated that the drawings are illustrative and not limiting of the scope of the invention which is defined by the appended claims. The embodiments shown accomplish various aspects and objects of the invention. It is appreciated that it is not possible to clearly show each element and aspect of the invention in a single FIGURE, and as such, multiple figures are presented to separately illustrate the various details of the invention in greater clarity. Similarly, not every embodiment need accomplish all advantages of the present invention.

DETAILED DESCRIPTION

The invention and accompanying drawings will now be discussed in reference to the numerals provided therein so as to enable one skilled in the art to practice the present invention. The drawings and descriptions are exemplary of various aspects of the invention and are not intended to narrow the scope of the appended claims.

As used herein, the term "ferromagnetic," "ferromagnet," and "ferromagnetism" refers to substances such as iron, nickel, cobalt, etc. and various alloys that exhibit high magnetic permeability, a characteristic saturation point, and magnetic hysteresis.

Figure 1:
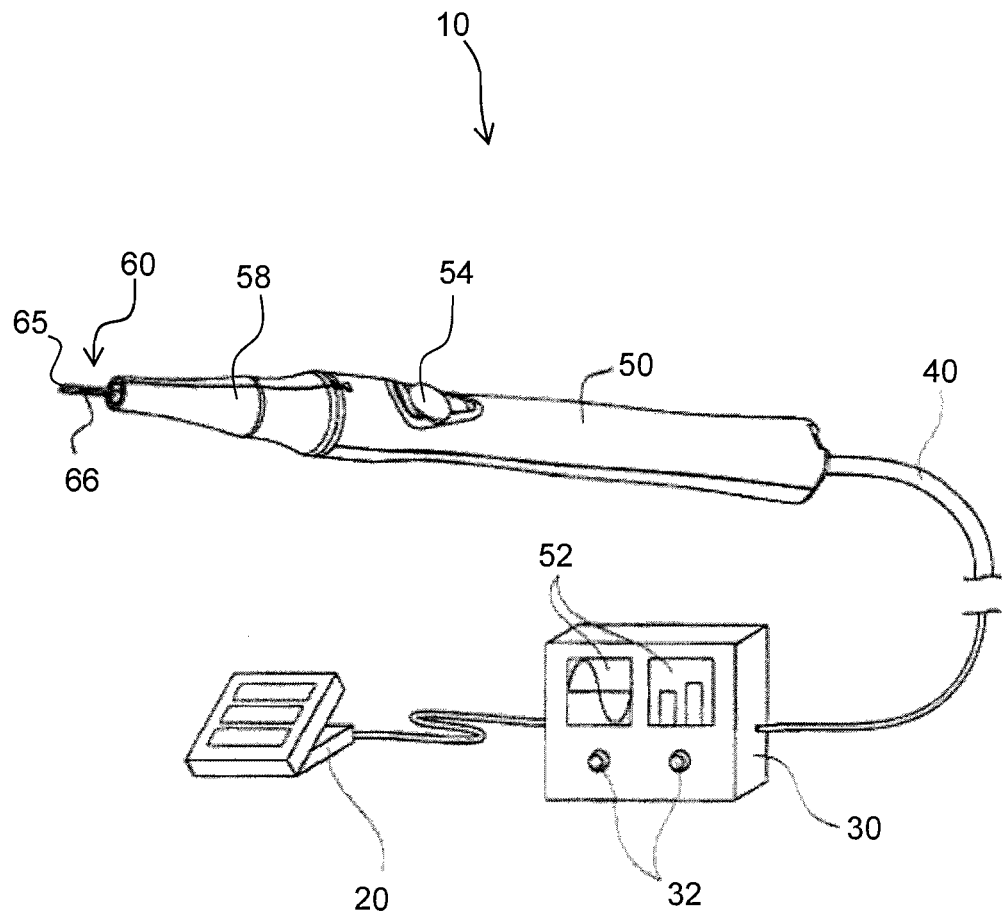
FIG. 1 shows a perspective view of a thermal surgical instrument system in accordance with the principles of the present invention.
Figure 2:
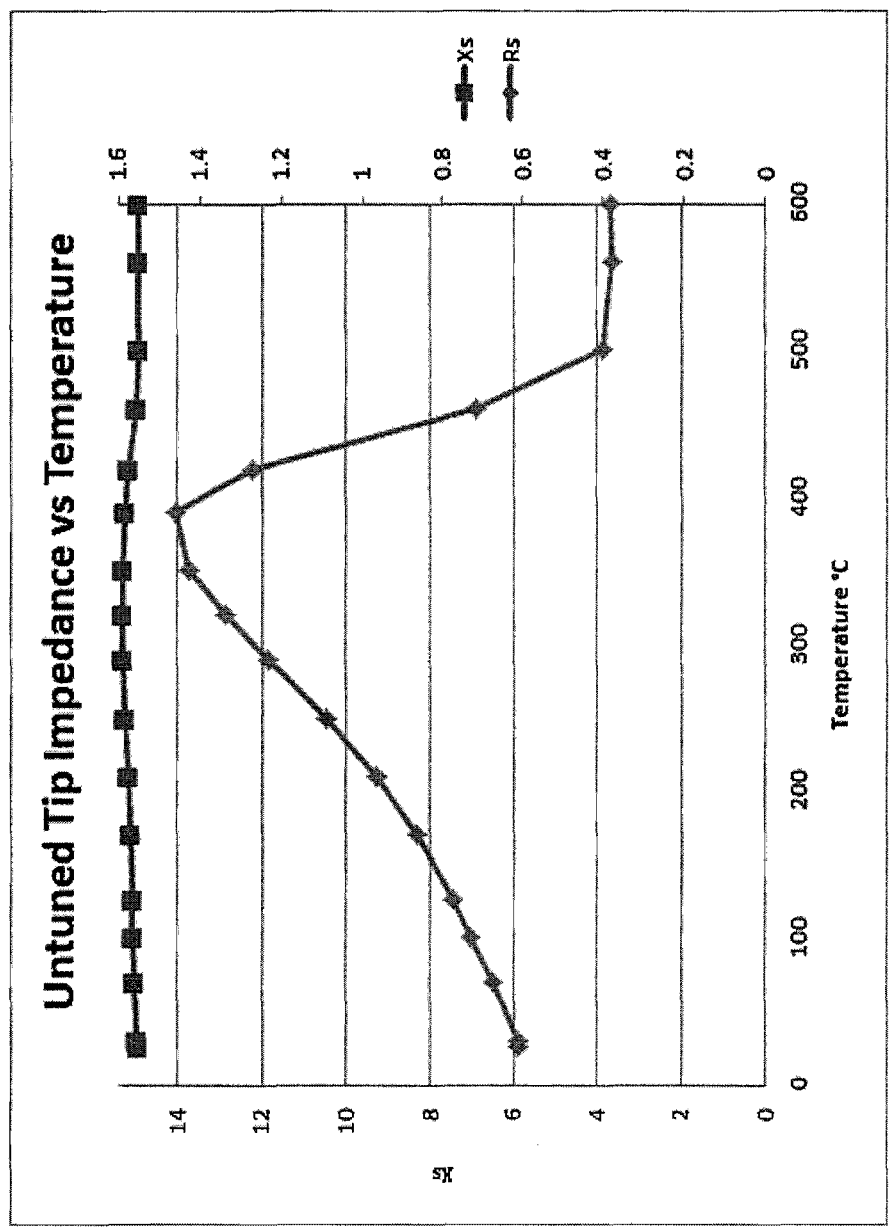
FIG. 2 shows a graphical representation of the impedance of a thermal element as its temperature is increased.
Figure 3:
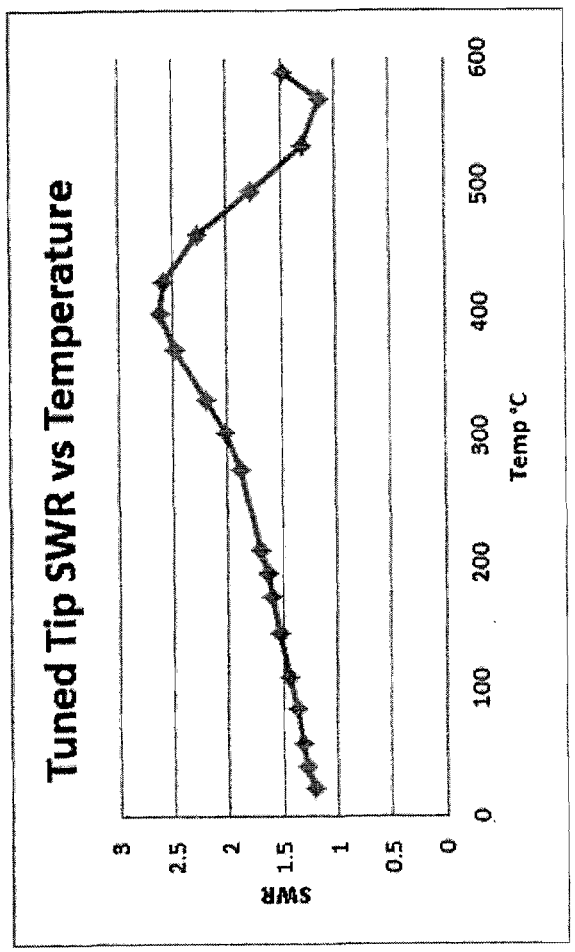
FIG. 3 shows a graphical representation of the standing wave ratio of a thermal element as its temperature is increased.

Turning now to FIGS. 1 through 3, FIG. 1 shows a perspective view of a thermal surgical instrument system, generally indicated at 10. As will be discussed in additional detail below, the thermal instrument system 10 may use a conductor associated with a ferromagnetic material to treat or destroy tissue (e.g. endothelial tissue welding, homeostasis, ablation, etc).

It will be appreciated that the thermal surgical instrument 10 may use heat to incise tissue without the use of a sharp edge such as with a conventional scalpel. While the embodiments of the present invention could be made with a relatively sharp edge so as to form a cutting blade, such is not necessary as the heated coating discussed herein will separate tissue without the need for a cutting blade or sharp edge. However, for convenience, the term cutting is used when discussing separating tissue.

According to one aspect of the invention, the thermal surgical instrument system 10 may include one or more control mechanisms, such as one or more foot pedals 20 to control output energy produced by a power supply 30. The energy from the power supply 30 may be sent via radio frequency (RF) or oscillating electrical energy along a cable 40 to a body 50, such as a handpiece, having a thermal element 60, such as a ferromagnetic material 65 associated with a conductor 66. As shown in FIG. 1, the conductor 66 may be circumferentially coated or plated with the ferromagnetic material 65. The ferromagnetic material 65 may convert the electrical energy into available thermal energy such that heating is substantially uniform along the entire section of the ferromagnetic material 65 disposed on the electrical conductor 66, or "ferromagnetic region".

The RF energy may travel along the conductor's 66 surface in a manner known as the "skin effect". Skin effect is the tendency of an alternating electric current to become distributed within a conductor 66 such that the current density is highest near the surface of the conductor 66, and decreases with greater depths in the conductor 66. The electric current flows mainly at the "skin" of the conductor 66, between the outer surface and a level called the skin depth. The skin effect causes the effective resistance of the conductor 66 to increase at higher frequencies where the skin depth is smaller, thus reducing the effective cross-section of the conductor 66. The skin effect is due to eddy currents induced by the changing magnetic field resulting from the alternating current. The skin depth is a function of the electrical resistivity, the magnetic permeability of the material conducting the current, and the frequency of the applied alternating RF current. For example, at 60 Hz in copper, the skin depth is about 8.5 mm. At high frequencies the skin depth becomes much smaller.

Over 98% of the current will flow within a layer 4 times the skin depth from the surface and virtually all of the current is within the first 5 skin depths. This behavior is distinct from that of direct current which usually will be distributed evenly over the cross-section of the conductor 66. The skin depth of a conductor 66 may be expressed by the following equations:

$$\delta = \sqrt{2\rho/\omega\mu} = 1/\sqrt{\pi f \mu \sigma}$$

Where:
$\delta$=skin depth (or penetration depth)
$\rho$=resistivity of the conductor
$\omega$=angular frequency of current
$\mu$=absolute magnetic permeability of conductor
$\sigma$=conductivity of the conductor
f=frequency The current density in the conductor 66 may be expressed by the following equation:

$$J = J_s e^{-d/\delta}$$

Where
$J_s$=the current at the surface of the conductor
$\delta$=skin depth (or penetration depth
d=depth from the surface of the conductor The flow of current through the conductor 66 may also create a magnetic field which may act on the ferromagnetic material 65 having an open loop B-H curve (also known as an open hysteresis loop), resulting in hysteresis losses and resultant thermal energy. For example, electrodeposited films, such as a nickel-iron coating like PERMALLOY™, may form an array of randomly aligned microcrystals, resulting in randomly aligned domains, which together may have an open loop hysteresis curve when a high frequency current is passed through the conductor 66.

As the domains realign with each oscillation of the current, the ferromagnetic material 65 will heat due to hysteresis losses in the ferromagnetic material 65. Heating of the ferromagnetic portion 65 due to hysteresis loss ceases above its Curie point because the material loses its magnetic properties as explained in more detail below. Additionally, because the relative permeability of the ferromagnetic portion 65 changes in response to temperature, the associated skin depth also changes, and therefore the amount of current conduction through the skin layer undergoes a transition near the Curie point. Thus, heating of the ferromagnetic portion 65 due to resistive heating may also be reduced as it approaches the Curie point.

As mentioned above, the ferromagnetic material 65 may have a Curie temperature. A Curie temperature is the temperature at which the material becomes paramagnetic, such that the magnetic properties of the coating are lost. When the material becomes paramagnetic, the ferromagnetic heating may be significantly reduced or even cease. Theoretically, this should cause the temperature of the ferromagnetic material 65 to stabilize around the Curie temperature if sufficient power is provided to reach the Curie temperature. However, it has been found that the temperature of the ferromagnetic material 65 may exceed its calculated Curie temperature under certain operational conditions. It has been observed that if sufficient power has been applied, the tip temperature can continue to rise due to resistive heating in the overall conductor and the tip can potentially exceed the Curie temperature. When this occurs, an increase in current is observed while operating at a constant power level. It is believed that this may be due, at least in part to an increase in the skin depth and a resulting drop in impedance above the Curie temperature. The increase may also be due to the resistance of the ferromagnetic coating dropping which in turn raises the current level for a fixed power level. The increased current may then cause more resistive heating in the non-ferromagnetic portion of the conductor. Thus, it may be preferable to use an underlying conductor having high electrical conductivity.

Therefore, passage of alternating electrical energy through the conductor's 66 surface may cause Joule heating (also known as ohmic heating or resistive heating) along the thermal element 60. As the alternating electrical energy passes into the ferromagnetic region the current may jump to the ferromagnetic material 65 disposed on the conductor. Thus, a significant portion of the thermal energy created in the ferromagnetic material 65 may be due to Joule heating. Also, the RF energy may be converted into thermal energy in the ferromagnetic region due to hysteresis losses in the ferromagnetic material 65.

A thermal element 60 may be constructed so that the ferromagnetic material 65 has a thickness corresponding to approximately 5 skin depths such that substantially all of the alternating electrical energy flowing through the conductor 66 jumps to the ferromagnetic coating 65. As skin depth is a function of the frequency of the alternating electrical energy passing through the conductor 66 and/or ferromagnetic material 65, the thickness of the ferromagnetic material 65 needed to achieve approximately 5 skin depths may vary depending on the frequency of the alternating electrical energy being delivered to the conductor 66. For example, by delivering a high frequency alternating electrical energy to the conductor 66 a thin layer of ferromagnetic material 65 is sufficient to provide for substantially all of the alternating electrical current to jump to the ferromagnetic material 65. According to one aspect of the invention, a thermal element 60 may be constructed of a 0.5 mm diameter conductor wire having a 10 μm layer of PERMALLOY™ disposed thereon, such that delivering an alternating electrical current having a frequency of 40.68 MHz to the conductor wire will cause substantially all of the alternating electrical current to jump to the PERMALLOY™ layer.

The RF conductor from the signal source up to and including the tip may form a resonant circuit at a specific frequency (also known as a tuned circuit). Thus, when alternating electrical current is delivered to the conductor 66 the standing wave ratio ("SWR") of the circuit will be approximately 1 at room temperature. As the thermal element 60 heats up, the impedance of the thermal element 60 changes, thereby changing the overall circuit impedance. Monitoring the impedance of the circuit, either directly as shown in FIG. 2, or indirectly, provides information related to the temperature of the thermal element 60. Thus monitoring the impedance of the circuit can be used to control the temperature of the thermal element 60. Furthermore, the impedance change in the circuit also affects the amount of reflected power and thus changes in the SWR may also be monitored (as shown in FIG. 3) and used to control the temperature of the thermal element 60. Thus, for example, the temperature of the thermal element 60 may be controlled to a specific temperature within a range of about plus or minus 30° Centigrade, or preferably, to a temperature within a range of about plus or minus 20° Centigrade, or more preferably to a temperature within a range of about plus or minus 10° Centigrade, or even more preferably to a temperature within a range of about plus or minus 5° Centigrade.

One advantage achieved by the ferromagnetic heating is that the ferromagnetic material 65 can be heated to a cutting temperature rapidly. In some instances the ferromagnetic material 65 can be heated in a small fraction of a second (e.g. as short as 100 ms). Additionally, because of the relatively low mass of the ferromagnetic material 65, the small thermal mass of the conductor 66, and the localization of the heating to a small region due to construction of the body 50, the material may also cool extremely rapidly (e.g. in some instances in approximately one half of a second). This provides a surgeon with a precise thermal instrument while reducing accidental tissue damage caused by touching tissue when the thermal instrument is not activated.

It will be appreciated that the time period required to heat and cool the thermal element 60 will depend, in part, on the relative dimensions of the conductor 66 and the ferromagnetic coating 65 and the heat capacity of the structure of the surgical instrument. For example, the above exemplary time periods for heating and cooling of the thermal element 60 may be achieved with a tungsten conductor having a diameter of about 0.375 mm and a ferromagnetic coating of a Nickel Iron alloy (such as NIRON™ available from Enthone, Inc. of West Haven, Conn.) about the tungsten conductor about 0.010 mm thick and two centimeters long.

One advantage of the present invention is that a sharp edge may not be needed. When power is not being supplied to the surgical instrument, the instrument will not inadvertently cut tissue of the patient or of the surgeon if it is dropped or mishandled. If power is not being supplied to the conductor 66 and ferromagnetic material 65, the "cutting" portion of the instrument may be touched without risk of injury. This is in contrast to a sharpened cutting blade which may injure the patient or the surgeon if mishandled.

It should be understood that the surgical instrument 10 may include indicia of the power being applied and may even include a mechanism for controlling the power. Thus, for example, a series of displays 52 could be used to indicate power level or the body 50, such as a handpiece could include a switch, rotary dial, sets of buttons, touchpad or slide 54 that communicate with the power source 30 to regulate power and thereby affect the temperature at the ferromagnetic material 65 to having varying effects on tissue. The controls also may be included in the power supply 30, for example control dials 32 or the like, or even be included in a separate control instrument, such as a remote control. Other additions may also be placed on the handpiece 50, power supply 30, remote control, etc. in various locations.

The adjustability of the temperature of the ferromagnetic material 65 may provide the surgeon with precise control over the tissue effects that may be achieved through use of the surgical instrument 10. Tissue effects such as cutting, hemostasis, tissue welding, tissue vaporization and tissue carbonization occur at different temperatures. By including a user control to adjust the power output, the surgeon (or other physician, etc.) can adjust the power delivered to the ferromagnetic material 65 and consequently control the tissue effects to achieve a desired result.

Additionally, power delivery to the thermal body 50 may be controlled by varying the amplitude, frequency or duty cycle of the alternating current waveform, or alteration of the circuit to affect the standing wave driving the ferromagnetic coated conductor, which may be achieved by input received by a foot pedal 20, the controls on the power supply 30, or handpiece 50, etc.

Furthermore, as described in more detail below, the surgical instrument 10 may be comprised of a handpiece 50 which can removably receive a thermal element 60. For example, various removably attachable surgical tips 58 may have a different thermal elements 60 (e.g. differing in size, shape, etc.) associated therewith. Thus, thermal elements 60 of various configurations may be used with the handpiece 50.

Figure 4:
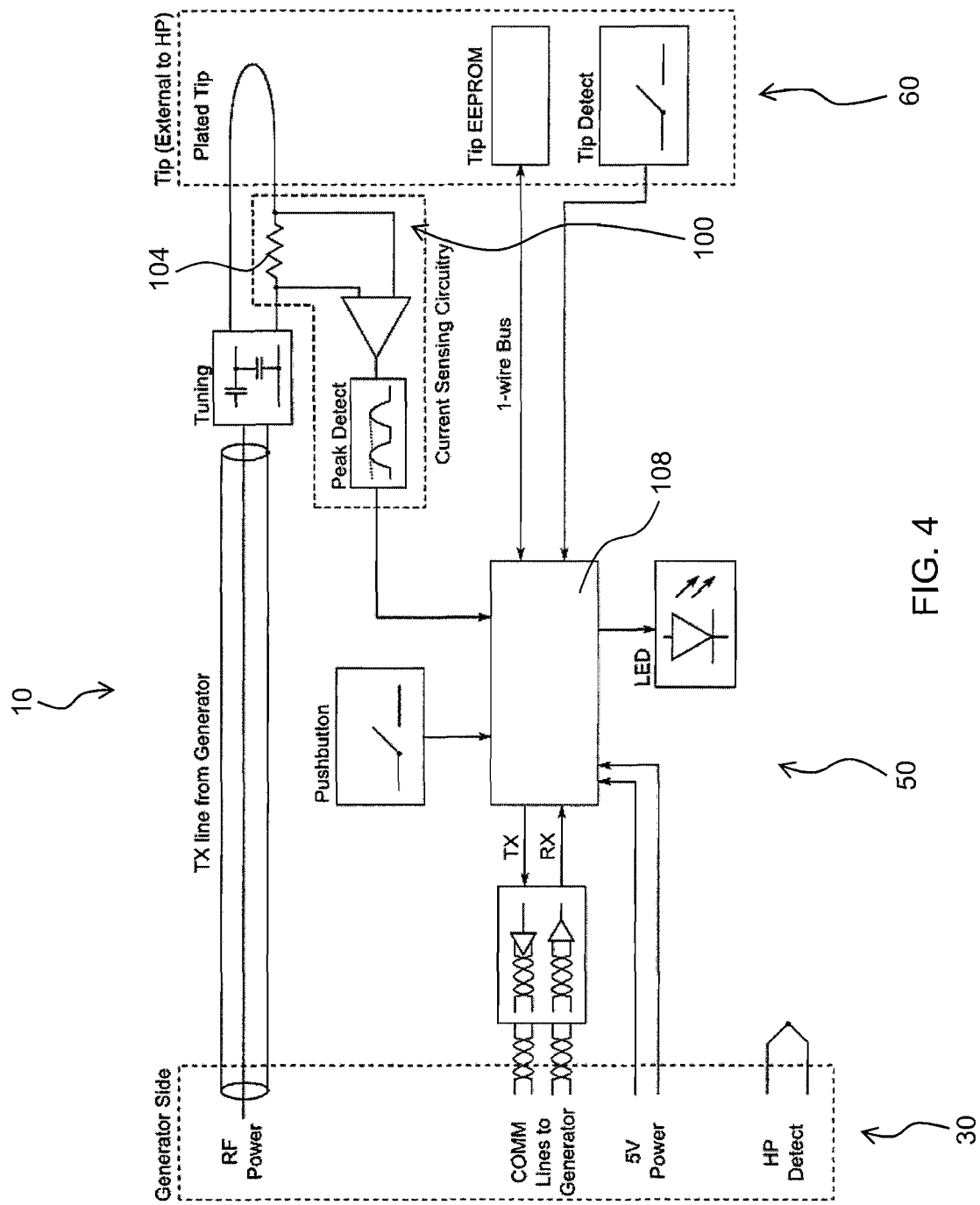
FIG. 4 shows a block diagram of a thermal surgical instrument of the present invention.

Turning now to FIG. 4, a block diagram of the thermal surgical instrument 10 of the present invention is shown. The handpiece 50 may be responsible for current sensing, temperature sensing, impedance sensing, etc. Data collected from the thermal element 60 may be sent to a power supply 30 on a substantially continuous basis. For example, data may be sent to supply microprocessor at short intervals of about 10 milliseconds.

The one or more sensing circuits may be used to monitor various behavior characteristics of the thermal element 60 when in use, such as how much current is delivered to the thermal element 60, the impedance of the circuit, etc., or a combination of behavior characteristics of the thermal element 60. For example, the peak-detection device 100 may determine the current which is delivered to the tip 60 by measuring the voltage drop across a resistor 104 (e.g., circuit-board trace in the tip or a corresponding resistor in the handpiece or power supply), which may be directly in-line with the current flowing to the tip. The voltage drop is directly proportional to the current in the branch of the circuit by Ohm's Law (V=IR). The higher the voltage, the more current there is flowing through the branch. The voltage across the resistor 104 may be passed back through a peak-detection circuit to track the peaks of the signal, such as the peaks of a 40.68 MHz signal, within its operational range.

Moreover, the sensing circuitry may detect the impedance of the thermal element 60, thus providing feedback as to the temperature of the thermal element (See e.g. FIGS. 2 and 3). The output of the circuit may be a DC voltage, which is fed into a converter 108, such as a microcontroller, Analog-to Digital converter ("DAC"), microprocessor, etc., and digitized. This data may be sent on a substantially continuous basis to the power supply 30 and may be used in a power control algorithm. It will be appreciated that one or more sensing circuits may be located at various locations in a thermal surgical instrument system of the present invention, such as a control console, the handpiece, a removable surgical tip, a remotely located unit, etc.

Sensing various properties of the thermal element 60 may be necessary because of the nature of the high permeability (high-mu) of the ferromagnetic material 65 on the tip 60. It is currently believed that, during normal operation, the majority of the current flow through the ferromagnetic material 65 may be attributed to the skin effect. When too much current flows through the ferromagnetic material 65, the Curie temperature may be reached and the permeability of the ferromagnetic material 65 may drop off dramatically. Consequently, the current begins to flow more significantly through the conductor 66 reducing the resistance in the thermal element 60. As the resistance is decreased at a constant power level, the current will increase and the voltage across the sensing resistor 104 will also increase. Thus, it is currently believed that as the Curie temperature is reached or exceeded that the skin depth increases, contributing to a decrease in the resistance of the heated tip 60. It has been observed that an increase in current occurs as the Curie temperature is exceeded at a constant power level.

Figure 5:
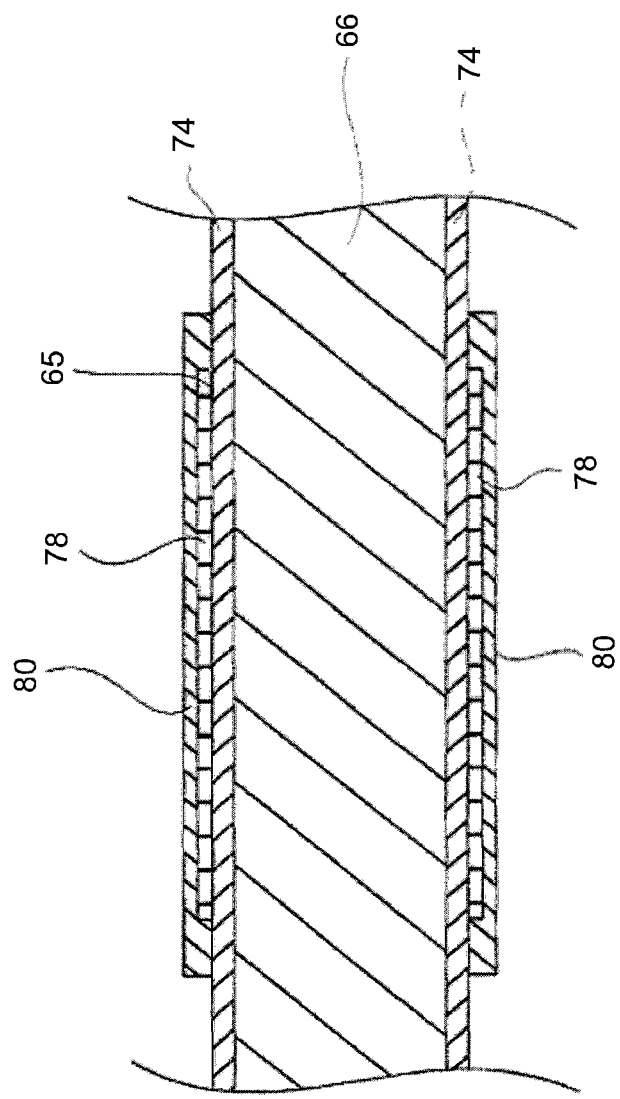
FIG. 5 shows a close-up, cross-sectional view of one thermal element of the present invention.

Turning now to FIG. 5, there is shown a cross-sectional view of a portion of a surgical tip having a conductor 66, such as a conductor wire, in accordance with one aspect of the invention. It may be desirable that the conductor 66 have a relatively small diameter or cross-section so as to make precise cuts in tissue, or other materials. However, it is also may be desirable to have the conductor 66 be relatively stiff and resist bending when encountering tissue. Examples of metals having this property may include tungsten, titanium, stainless steel, Haynes 188, Haynes 25, etc.

Other properties of the material used for the conductor 66 may be important. These properties may include the resistivity of the material, the thermal and electrical conductivity of the material, the material's heat capacity, the material's coefficient of thermal expansion, the annealing temperature of the material, and the ability to plate a second material to the material comprising the conductor 66.

In choosing a material to use as the conductor 66, it may be important that such material have the greatest amount of resistance to bending while having low resistivity to minimize heating of the conductor 66 due to resistance heating. Additionally, it may also be important that the material have a low heat capacity so that heat is not stored in the conductor 66 thus allowing the surgical tip to cool rapidly when not being used. This may help limit or prevent collateral damage to structures adjacent the surgical site.

Additionally, it is desirable that the conductor 66 be comprised of material having a sufficiently high annealing temperature. At times, the surgical tip may be operated at temperatures, for example, between about 400 degrees Celsius and 500 degrees Celsius. Thus, to avoid alterations in the properties of the conductor 66, the annealing temperature of the material used as the conductor should be sufficiently higher than the expected operating ranges of the surgical tip.

Furthermore, it may be desirable that the support 70 be comprised of a material having a coefficient of thermal expansion value that is close to the coefficient of thermal expansion of the ferromagnetic material 65, such as a ferromagnetic coating 78, to facilitate plating of the ferromagnetic coating 78 to the conductor 66 in some configurations.

It has been observed, however, that some materials having adequate resistance to bending (Young's modulus) during normal operation of the surgical tip may have a coefficient of thermal expansion that is too low for adequate plating integrity. Thus, one or more intervening layers 74 having an intermediate coefficient of thermal expansion may be plated on the conductor 66 and then the ferromagnetic layer or coating 78 plated on the one or more intervening layers 74 to provide for a transition to accommodate the difference between the coefficients of thermal expansion of the support 70 and the ferromagnetic material 65.

Another important factor regarding the material used for the conductor 66 may be its ability to conduct electricity. There are multiple materials which provide adequate support, but which are not sufficiently conductive. Thus a conductor 66 may be comprised of multiple layers of different material so as to minimize any undesirable property or properties of the conductor 66.

For example, the conductor 66 may have a one or more conductive intervening layers 74 disposed thereon, such as copper, silver, etc. or other conductive material. The intervening layer 74 allows the energy to pass without significant resistive heating, thus allowing the tip to cool down more rapidly. (It will be appreciated that the cross-sectional view of FIG. 5 is not necessarily to scale and the support may be much larger in diameter than the thickness of the other layers discussed herein. Moreover, it will be appreciated that the conductive intervening layer 74 may extend the entire length of the conductor 66).

The conductor 66 of FIG. 5 also shows a ferromagnetic layer or coating 78 disposed adjacent to the intervening layer 74. The ferromagnetic layer or coating 78 may be plated on the intervening layer 74. The ferromagnetic coating 78 may be located along a portion of the conductor 66 at a defined location (or locations) so as to provide for localized heating along the surgical tip only in an area where heating is desired. For example, the ferromagnetic layer or coating 78 may be located along less than about 90%, 50%, 10%, etc. of the length of the conductor 66 so as to provide localized heating in a desired area. In other words, the length which the ferromagnetic material extends may be less than the length of the conductor 66. The ferromagnetic coating 78 may have high permeability to facilitate inductive or other ferromagnetic heating of the ferromagnetic material, such as NIRON™, PERMALLOY™, Co, $CrO_2$, etc. Additionally, the ferromagnetic coating 78 may have a relatively high thermal conductance and low heat capacity to facilitate rapid heating and cooling of the surgical tip.

The ferromagnetic coating 78 may be exposed or may be covered with an exterior coating 80 made from a biocompatible material to ensure that there is no reaction between the ferromagnetic coating 78 and the patient tissues. The exterior coating 80 may also act as a lubricant between the surgical tip and tissue which is being treated by reducing the attachment of biologic tissues to the surgical tip. For example, the exterior coating 80 may be titanium nitride (or one of its variants), TEFLON or a host of other biocompatible materials.

The exterior layer 80 may also act as an oxygen barrier to prevent oxidation of the layer of ferromagnetic material 65, any intervening layer 74, and/or the support 70. For example, it has been observed that oxidation of the support 70 may cause the support 70 to become brittle making the support 70 more susceptible to damage. It will be appreciated that the exterior layer 80 may be disposed on the conductor 66 so as to substantially cover the ferromagnetic material and the entire conductor 66. Alternatively, the exterior layer may be disposed on the conductor 66 so as to cover the ferromagnetic coating 78 and only a portion of the conductor 66.

According to one aspect of the invention, a thermal element 60 may comprise a conductor having an intermediate layer having a cross-sectional thickness corresponding to about 2-5 skin depths and a ferromagnetic layer having a cross-section thickness also corresponding to about 2-5 skin depths. For example, a thermal element 60, such as the one shown in FIG. 5, receiving oscillating electrical energy having a frequency of 40.68 MHz may comprise a conductor 66 having a diameter of about 500-750 μm, a copper intervening layer 74 having a cross-sectional thickness of about 20-50 μm, and a ferromagnetic material 65 (e.g. a coating or layer 78) having a cross-sectional thickness of about 2-10 μm. The thickness of the ferromagnetic material 65 forming the layer or coating 78 may be selected as a function of the skin depths of the conductor 66 and/or intervening layers 74, or the combined skin depths of the conductor 66 and/or multiple intervening layers 74 if such are included in a surgical tip. The antioxidation layer may be very thin, such as 1-3 μm.

It will be appreciated that thermal elements of the present invention may include a ferromagnetic layer having a cross-section thickness corresponding to greater than 5 skin depths. Controlling the temperature of the thermal element may reduce the range of temperatures that the thermal element is subject to as compared to the more extreme thermal cycling that the thermal element would experience if temperature was not limited. Because controlling the temperature of the thermal element reduces such extreme thermal cycling, a thermal element used according to principles of the present invention may have better structural integrity. Thus, in addition to thin layers of ferromagnetic material 65 plated on the conductor, ferromagnetic sleeves and solid ferromagnetic heating elements may be used.

The thermal element 60 (or tips) may be coupled to a base, shroud, etc. 58 (FIG. 1) which may be configured to be removably received by a handpiece 50. The tip 60 may also include a computer storage device, such as an electrically erasable programmable Read-only Memory ("EEPROM") device, to store certain configuration parameters associated with a particular tip 60 and transmit those configuration parameters to a microprocessor in the surgical handpiece 50 or power control system 30 (See e.g. FIG. 1). When power is delivered to the conductor 66, the ferromagnetic material 65 may heat according to the power delivered. Because of the small thickness of ferromagnetic material 65, it may heat very quickly (e.g. a small fraction of a second) when the current is directed through the conductor 66, and cool down quickly (e.g. a fraction of a second) when the current is stopped.

It will be appreciated that various thermal elements 60 may be constructed such that different thermal elements have a different size, shape, etc., for use in a particular surgical procedure, and/or are configured to be used in association with a particular surgical device.

Figure 6A:
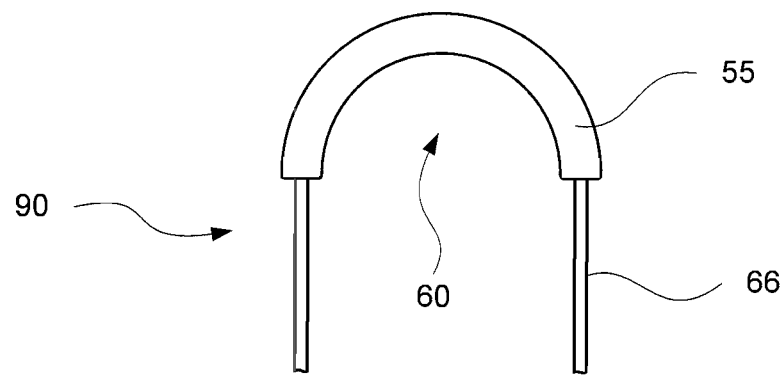
FIG. 6A shows a side view of a thermal element forming a dissecting loop.
Figure 6B:
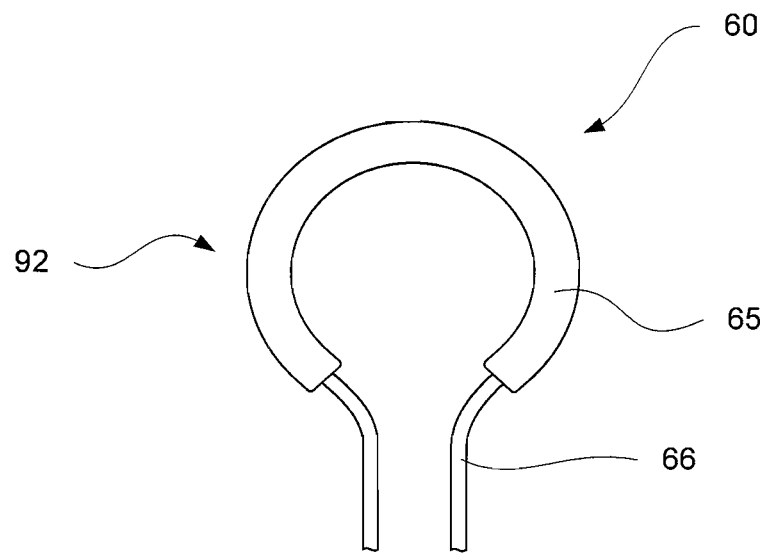
FIG. 6B shows a side view of a thermal element forming a resecting loop.

For example, FIG. 6A shows a dissecting loop and FIG. 6B shows a resecting loop. FIGS. 6A and 6B are shown to illustrate the different shapes and sizes of thermal elements of the present invention and are not intended to limit the scope of the invention. Additionally, FIGS. 6A and 6B illustrate that the ferromagnetic material 65 may extend along the conductor 60 at various length, as the dissecting loop may have a shorter length of ferromagnetic coating disposed on the conductor 60 as compared to the length of the ferromagnetic material 65 disposed on the conductor 60 of the resecting loop.

Figure 7A:
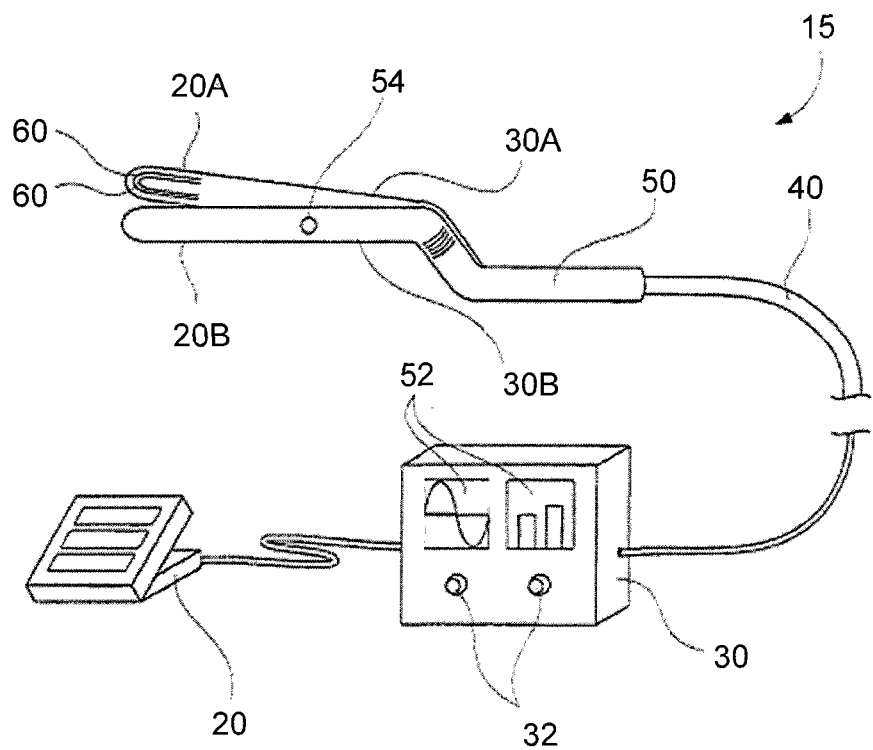
FIG. 7A shows a perspective view of another thermal surgical instrument system in accordance with the principles of the present invention.

Also, thermal elements 60 of the present invention may be disposed on, or embedded in, a surface of a surgical instrument, rather than in a standalone configuration. For example, thermal elements 60 may be constructed for use with a sealing and cutting instrument 15 as shown in FIG. 7A. In use, the sealing and/or cutting instrument 15 has a body 50 comprising tips 20A, 20B which may be placed around or on opposing sides of a duct or tissue to be sealed. The tips 20A and 20B may be placed at the end of arms 30A, 30B which are held in a user's hand. A user may squeeze the arms 30A, 30B of the instrument together causing the tips 20A, 20B to provide pressure on the duct or tissue. Electrical energy may then be directed to one or more of the thermal elements 60 on tip 20A and/or 20B to heat the thermal element 60. (It will be appreciated that the active element could be applied hot to the duct, or could by applied and then heated). The heat generated in the active element is applied to the duct or tissue to cause the duct or tissue to seal. In accordance with one aspect of the invention, a second energy level may be applied to a second thermal element 60 to heat the second thermal element 60 to a second temperature that is sufficient to cut the duct or tissue apart.

Figure 7B:
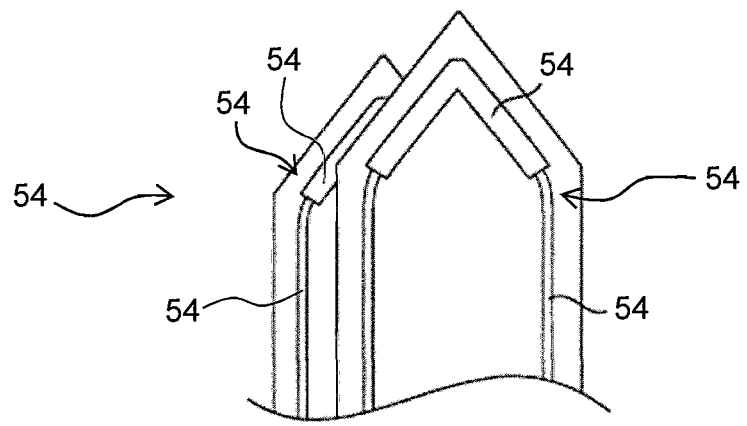
FIG. 7B shows a perspective view of a forceps with thermal elements disposed thereon.
Figure 7C:
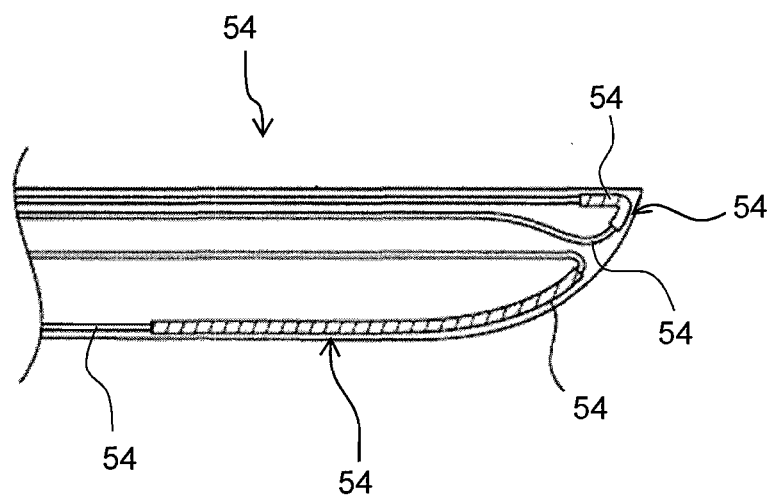
FIG. 7C shows a side view of a scalpel with thermal elements disposed thereon.

FIGS. 7B and 7C show examples of additional surgical instruments having one or more thermal elements 60 disposed on a surface thereof. FIG. 7B shows thermal elements 60 disposed forceps and FIG. 7C shows thermal elements 60 disposed on a scalpel. It will be appreciated that one or more thermal elements 60 may be disposed on other surgical instruments not shown so as to provide for treating a tissue in a surgical site with heat generated by the thermal element 60.

Furthermore, each class of thermal elements 60 (e.g. 2 mm dissecting loop (FIG. 6A), 4 mm resecting loop (FIG. 6B), sealing and cutting elements (FIG. 7A), etc.) may be characterized by its behavior under controlled conditions. The following information may be gathered and used to create power control algorithm constants, or configuration parameters, for each class of thermal element 60. These power control constants may include, for example, the following: the highest control power in air that prevents the tip from exceeding the Curie point; the tip current at which the tip reaches the Curie point when held in air; and the SWR at which the average tip is operating in air at a given power level. Using this information, a profile for each class of tips 60 may be developed and saved as a file, for example a tip configuration file (.tcf). As tips 60 are manufactured they may be baselined using the .tcf—this baseline information may be stored to the tip, for example, in the EEPROM and used by software and/or hardware disposed in communication with a surgical instrument system to specify a particular power control algorithm for the particular tip when a body 50 and active element 60 are connect to the power supply 30, such that power delivery to the active element 60 is appropriately controlled during use of the surgical instrument 10.

Tip configuration parameters or constants may include the following:

| Parameter | Description |
| --- | --- |
| Tip Type | Type of tip. For example:<br>2 mm dissecting loop<br>4 mm resecting loop<br>3 mm stout dissecting loop |
| Tip Configuration information | System settings specific to the tip. |
| Calibration information | Specific details on the performance of the tip |
| Limit information | SWR, current, temperature, etc. limit used by power control algorithm |
| Air Control Power | Power setting to use for algorithm "Air" state. |
| Max Power Setting | Maximum power settings available for the current tip |
| Cool-down time | Time (in seconds) until the tip is cool after energy has been removed |

One or more of the foregoing parameters may be used by a power control system to deliver a desired power to the instrument in a consistent manner, prevent the thermal element 60 of the surgical instrument from exceeding the Curie point, and/or prevent overheating of the thermal surgical instrument or heating of the instrument at locations other than the desired location. The power control system may include software having a power control algorithm module and/or hardware which may be used independently or in conjunction to control power delivery to the instrument.

Figure 8:
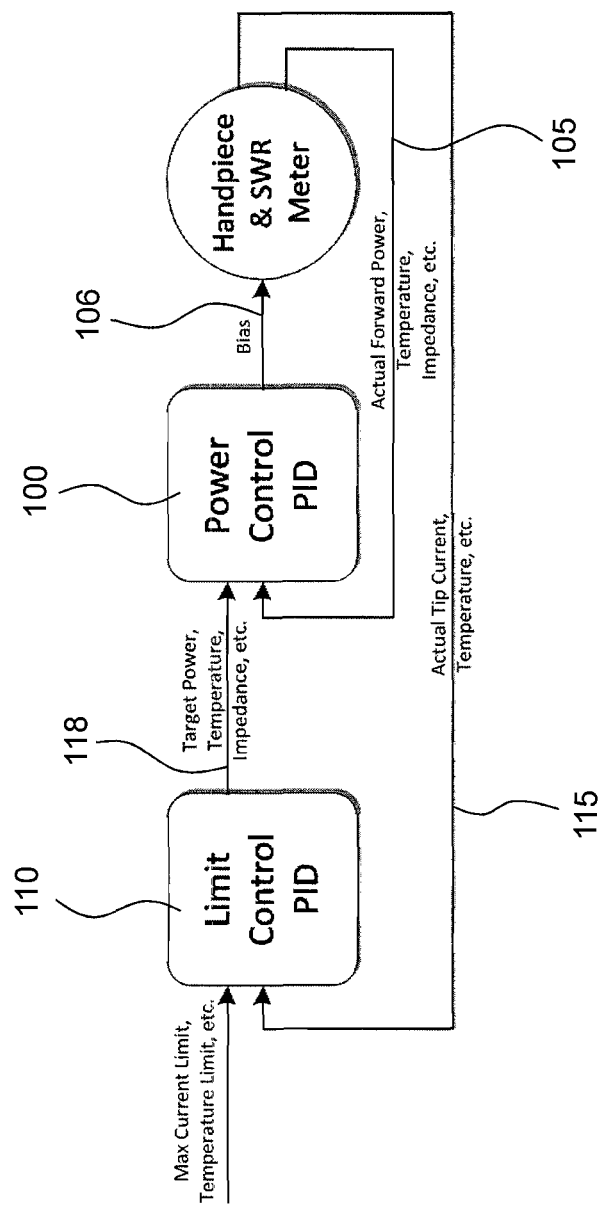
FIG. 8 shows a block diagram of cascaded PID controllers.

Consistent power delivery may be achieved with the use of a control loop feedback mechanism. The feedback mechanism may include one or more proportional-integral-derivative controllers (PID controller). For example, FIG. 8 shows a block diagram of cascaded PID controllers. The inner PID controller 100 may use the forward power (indicated by arrow 105) as its input feedback parameter, and outputs a bias voltage (indicated by arrow 106) as a control. The inner PID controller 100 may be tuned by power level, and may not require the use of the derivative constant (i.e. controller 100 may be a PI controller). The outer PID controller 110 may use tip current (indicated by arrow 115) as its input feedback, and output a target power (indicated by arrow 118) level to the inner PID 100. (The outer PID controller may use only the proportional constant or the proportional and integral constants). The combination of these controllers may provide a consistent control at the target power, without exceeding the maximum tip current.

While FIG. 4 primarily shows control of the temperature of the surgical tip based on forward power, the tip temperature may also be controlled by monitoring the reflected power, the standing wave ratio, or by measuring and controlling the net power (the forward power minus the reflected power), etc. According to one aspect of the invention, the temperature of a thermal element may be controlled by regulating the amount of power delivered to the thermal element such that the element does not exceed its Curie temperature. According to another aspect of the invention, the temperature of a thermal element may be controlled by regulating the amount of power delivered to the thermal element such that the element substantially maintains a more specific temperature desired by the user.

Figure 9:
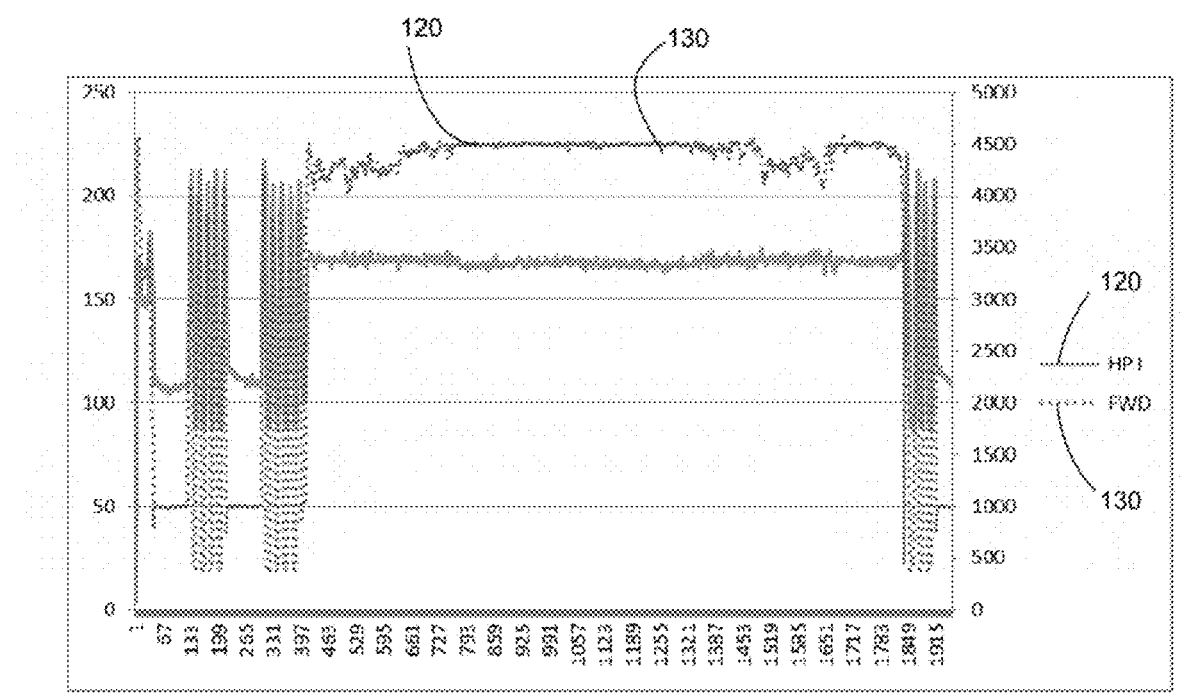
FIG. 9 shows a graphical representation of one example of the current limiting effects when using cascaded PID controllers according to principles of the present invention.

For example, FIG. 9 shows a graph of an example of the current limiting effects when using cascaded PID controllers according to principles of the present invention. Note that the current (HP-I) 120 remains constant, while the forward power (FWD) 130 does not substantially exceed the set-point of 45 W (4500 on the right axis). Also, control of the power may be substantially maintained at 45 W while not being current limited.

Furthermore, preventing the tip from exceeding the Curie point may also be accomplished using the cascaded PID control of FIG. 8. As long as the tip current does not exceed the prescribed limit, the tip may perform as desired.

Additionally, heating of the tip 60 (FIG. 1) may be managed using a state machine as described below in connection with FIG. 10. Briefly, when the tip 60 is in a load (e.g. tissue), the heat generated may be principally dissipated into that load. However, when removed from the load the tip current immediately increases, and heat may be transferred back to the shroud 58 and subsequently the handpiece 50. The control algorithm may minimize the amount of time that the thermal element 60 is in air running at a high power level, without adversely affecting the responsiveness of the device and its readiness for use by the surgeon. Minimizing the power output of the surgical thermal element 60 when the device is not being used to treat tissue will minimize the heat transfer to the handpiece 50 and make the device more comfortable for the surgeon. Additionally, preventing overheating of the thermal element 60 and even lowering the temperature of the thermal element when the device is not used to treat tissue will prevent damage to the ferromagnetic material 65.

As mentioned above, a state machine may be designed to minimize the amount of power delivered to a thermal element 60 when it is in air and still provide the desired power to heat the ferromagnetic material 65 when in tissue. The particular challenge that this may present is the proper response of the instrument when physically moving between, for example, air and tissue. To overcome this challenge, the software may, for example, use the SWR as a trigger for determining the state of the tip (e.g. a high SWR indicates air, and a low SWR indicates a load).

According to one aspect of the invention, the surgical environment of the thermal element 60 may be determined by, for example, periodically sending a pulse of increase power to the thermal element and monitoring the affects, if any, on the behavior characteristics of the thermal element 60 (e.g. change in impedance, SWR, etc.). For example, if the thermal element 60 is well coupled to tissue then the temperature of the thermal element 60 will rise modestly (i.e. relatively low rate of change in current, impedance, SWR, etc.). If, however, the thermal element 60 is poorly coupled (i.e. the thermal element is in air), then the rate of change in the current, impedance, SWR, etc., will be high indicating that the thermal element is rapidly heating. If a high rate of change in the current, impedance, SWR, etc. is detected, then the power control system may drastically limit the amount of power delivered to the thermal element 60 to prevent overheating of the thermal element 60 and/or overheating at other locations which may be in thermal communication with the thermal element 60, such as the body or handpiece 50.

Limiting the amount of power delivered to the thermal element 60 to prevent overheating may also be important because the thermal element may be damaged when subjected to large temperature differential and/or extreme thermal cycling. For example, subjecting a thermal element to a large temperature differential can cause materials making up the thermal element to fracture, especially when heating the thermal element in air then contacting it with much cooler tissues or liquids. Thus, by limiting power delivery to the thermal element 60 and thereby limiting the temperature that the thermal element reaches, it may be less fragile when transitioning between, for example, air and liquid. (The use of ferrite beads and alloy mixes in ceramics have been examined as alternatives for generating heat. When excited by the magnetic field associated with high frequency current passing through a conductor, ferrite beads and alloy mixes in ceramics can reach high temperatures very quickly. However, one major problem with the use of these materials is that a large temperature differential can cause the material to fracture, especially when it comes into and out of contact with liquids. In other words, if a hot ferrite surgical instrument is quenched by a cooler pool of liquid, such as blood or other body fluids, the material's corresponding temperature drops rapidly and may cause the material to fracture. These fractures not only cause the tool to lose its effectiveness as a heat source, because the magnetic field is disrupted, but may require extraction of the material from the patient.)

Figure 10:
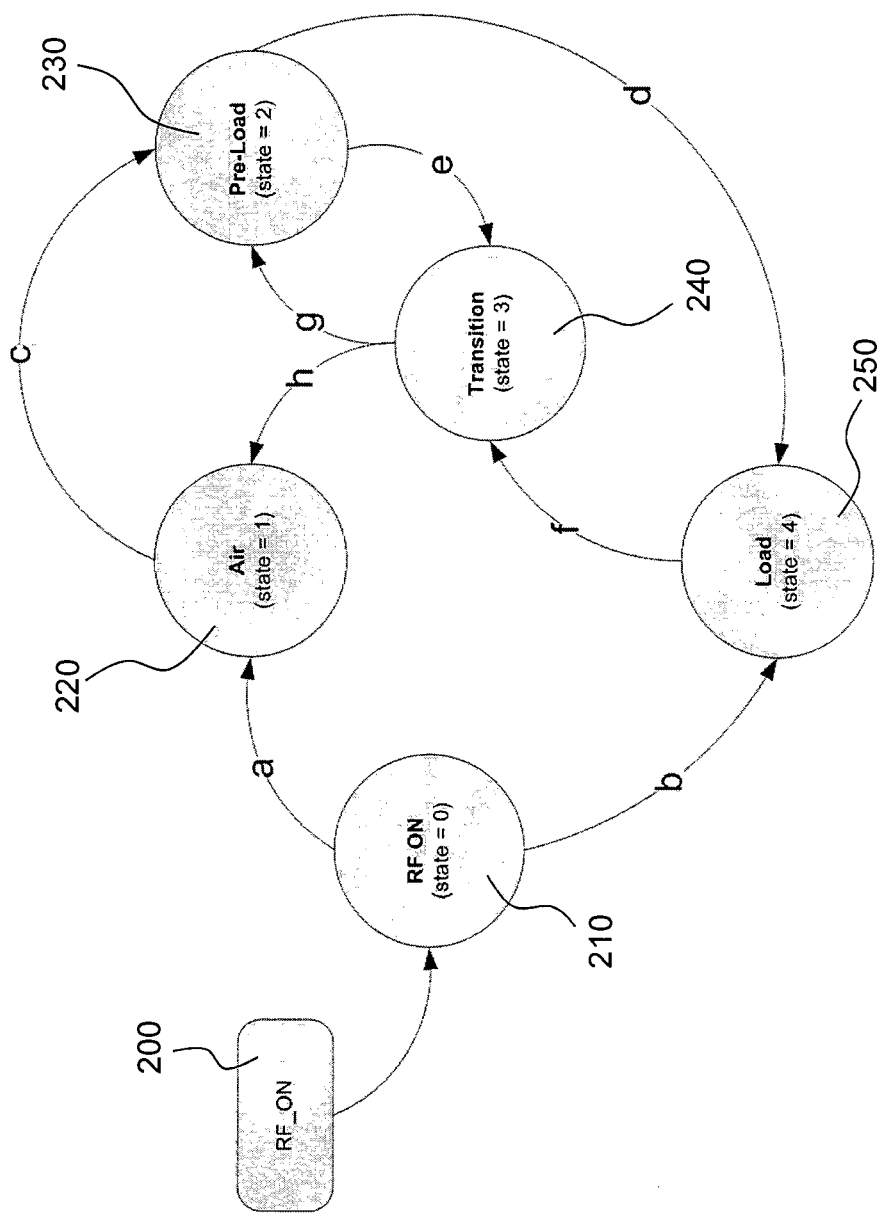
FIG. 10 shows a diagram a 5-stage state machine according to principles of the present invention.

Referring now to FIG. 10, there is shown a diagram a 5-stage state machine according to principles of the present invention. The descriptions of the state machine that follow may make use of "counts" to determine the length of stay in a given state. These counts may be incremented with each new sampling from an internal SWR meter. These samplings may be available, for example, every 4 milliseconds. Additionally, while in the Load state 250, to ensure valid power control, the software may periodically examine the internal power readings and compare these values to those read from the SWR meter. If a sizeable error exists (e.g. a difference of the greater of about 5 W or 20% of the commanded power) a power alarm may be displayed and the RF disabled.

When RF is first turned on, such as by a button press, foot pedal activation, etc, this may be referred to as the RF On state 210. Entry into RF On state 210 may set the control power target to the desired output level. Also, during the RF On state 210, the peak values for SWR and tip current may be monitored. The goal of this state may be to determine an initial condition for the tip 60 power. Some surgeons may activate the tip 60 in the air, and then touch tissue, while others may touch tissue, and then activate the tip 60. Thus, the RF On state 210 may allow the tip 60 to be fully powered in the event it is in contact with tissue when turned on or prevent the tip 60 from overheating if the tip is in the air by, for example, either current limiting the output power and/or only allowing the tip 60 to remain in the RF On state 210 for a short period of time.

From the RF On state 210, the tip 60 may enter either the Air state 220 or the Load state 250 depending on certain measured parameters. For example, the tip 60 may enter the Air state 220 when the peak SWR or tip current is too high for the target power setting. Alternatively if the peak SWR is in range for the target power after, for example, 125 counts (e.g. 500 ms) then the tip may enter the Load state 250. It will be appreciated that any particular duration a tip remains in a particular state described herein is being provided for illustrative purposes only. Thus, for example, according to one aspect of the invention the tip 60 may enter the Load state 250 from the Air state 210 if the peak SWR is in range from 250 counts, instead of 125 counts.

More specifically, the Air state 220 may be entered when indications point to the tip 60 not being in a load, e.g. not being in contact with a sufficient heat sink such as tissue. On entry into Air state 220, power may be set to low (as specified by a given tip's 60 parameters—e.g. 10 W for a 2 mm dissecting loop and a 4 mm resecting loop) to minimize tip heating. Exit from the Air state 220 may be via one of two primary methods, detection of a low SWR or a rapid decrease in reflected power (which may also be related to SWR, but a more dynamic indicator of change). To ensure that the Air state 220 is not exited prematurely (e.g. a sharp decline in the reflected power may also occur when decreasing the output power), the software may first wait until the slope of the reflected power has stabilized. Once stable, the SWR and slope of the reflected power may be monitored for exit conditions (described in more detail below).

To prevent the tip 60 from becoming stalled in the Air state 220 (or at a low power level) the state may automatically be periodically change from the Air state 220 to the Pre-Load state 230. For example, if the tip 60 is in the Air state 220 for more than one second, the state may be changed to the Pre-Load state 230 (described in more detail below) to more actively test the tip's 60 status. Changing the tip 60 to the Pre-Load state 230 should not significantly increase net power (e.g., with the power set to 60W and the tip 60 operating in air only, this active test method delivers an aggregate power of approximately 18.75W).

Exit conditions from the Air state 220 to the Pre-Load state 230 may include a slope of the reflected power which is stable for, for example, 5 counts (e.g. 20 ms); SWR which is less than the limit at low power; reflected power decreasing quickly (e.g. slope<–200); or about a one second time lapse.

The Pre-Load state 230 may be described as the stabilization state, and may be entered as a pre-condition to the Load state 250. On entry into the Pre-Load state 230, power may be set to the target value and the SWR monitored. The total duration in the Pre-Load state 230 may be between about 31 and 62 counts. For the first 31 counts (approximately 125 ms), the system may be allowed to stabilize with no regard to SWR limiting, allowing brief transitions outside of the allowable range while the power control stabilizes. For the remaining 31 counts, the SWR may be monitored for validity. Thus, even if the tip 60 is in air, it will have operated at the target power for only about 125 ms (as well as being current limited).

Additionally, rather than switch to the Air state 220 when the SWR is exceeded, the algorithm may make the assumption that the Pre-Load state 230 was entered with the intent of going to the Load state 250, and moves to the Transition state 240 instead.

From the Pre-Load state 230, the tip 60 may enter either the Load state 250 or the Transition state 240, depending on certain measured parameters. For example, the tip 60 may enter the Load state 250 when the SWR is within range for about 62 counts (approximately 250 ms). Alternatively, if the SWR exceeds the limit for the target power setting after about 31 counts, then the tip may enter the Transition state 240.

Referring more particularly to the Transition state 240, the Transition state 240 may be entered either from the Pre-Load state 230 or the Load state 250, and be used as an interim step to determine the current state of the tip 60, e.g. still in load, or back in air. On entry to the Transition state 240, the power may be set to the lowest level (e.g. 5 W) for the greater of 5 counts, or until the SWR drops below the target power SWR limit.

Therefore, the Transition state 240 may significantly decrease the power delivered to the tip 60 then, similar to the change to the Pre-Load state 230 from air, actively check the actively check the current state of the tip 60. If the SWR continues to exceed the limit for five successive attempts, it may be assumed that the tip 60 is in air, and the state may be changed accordingly, otherwise, the previous state (either Pre-Load 230 or Load 250) may be reset. Alternatively, the attempt counter may reset when more than one second has been spent in the Load state 250, as the power control algorithm may assume power stability at this point.

From the Transition state 240, the tip 60 may enter the Pre-Load 230 or the Air state 220, depending on certain measured parameters. For example, the tip 60 may enter Pre-Load state 230 when the tip 60 is in the Transition state 240 for at least 5 counts (20 ms) and SWR drops below the limit for the target power. The tip 60 may alternatively enter the Air state 220 if there are, for example, 5 consecutive attempts in the Transition state 240 without at least one second in the Load state 250.

The tip 60 may enter the Load state 250 from the Pre-Load state 230 when power is deemed stable and operating within the SWR limit, or re-entered from the Transition state when a determination is being made as to the current air/load status of the tip 60. The tip 60 may remain in the Load state 250, for example, until such time as the SWR increases past the limit for the target power level. More particularly, exit from the Load state 250 may occur when SWR exceeds the limit for the target power setting for 5 consecutive counts (approximately 20 ms).

The control algorithm is used to operate the power supply so as to maintain the tip 60 within a desired operation range in the particular state that the tip is currently in (e.g. in free air, in tissue, etc.). Thus, for a particular tip, the configuration parameters will determine operational characteristics such as temperature or power limits as well as operational or control parameters such as tuning impedance or reactance and the SWR constant. As discussed, the tip itself may have data stored therein on a storage device such as an EEPROM and provide that information to the power supply when the tip is connected to the surgical handpiece. Alternatively, the tip 60 may include an identification element such as a resistor whose value is different for different tip configurations and identifies the particular tip configuration. Thus, the power supply can sense the value of the resistor and determine from a table which tip configuration corresponds to that unique resistance value. The power supply itself can have the operational parameters of the different types of tips stored therein and use the identification element to determine which operational parameters should be used with the tip which has been connected to the surgical handpiece. It will be appreciated that the configuration parameters may be stored in alternate locations such as a computer or device which is separate from the power supply.

Figure 11:
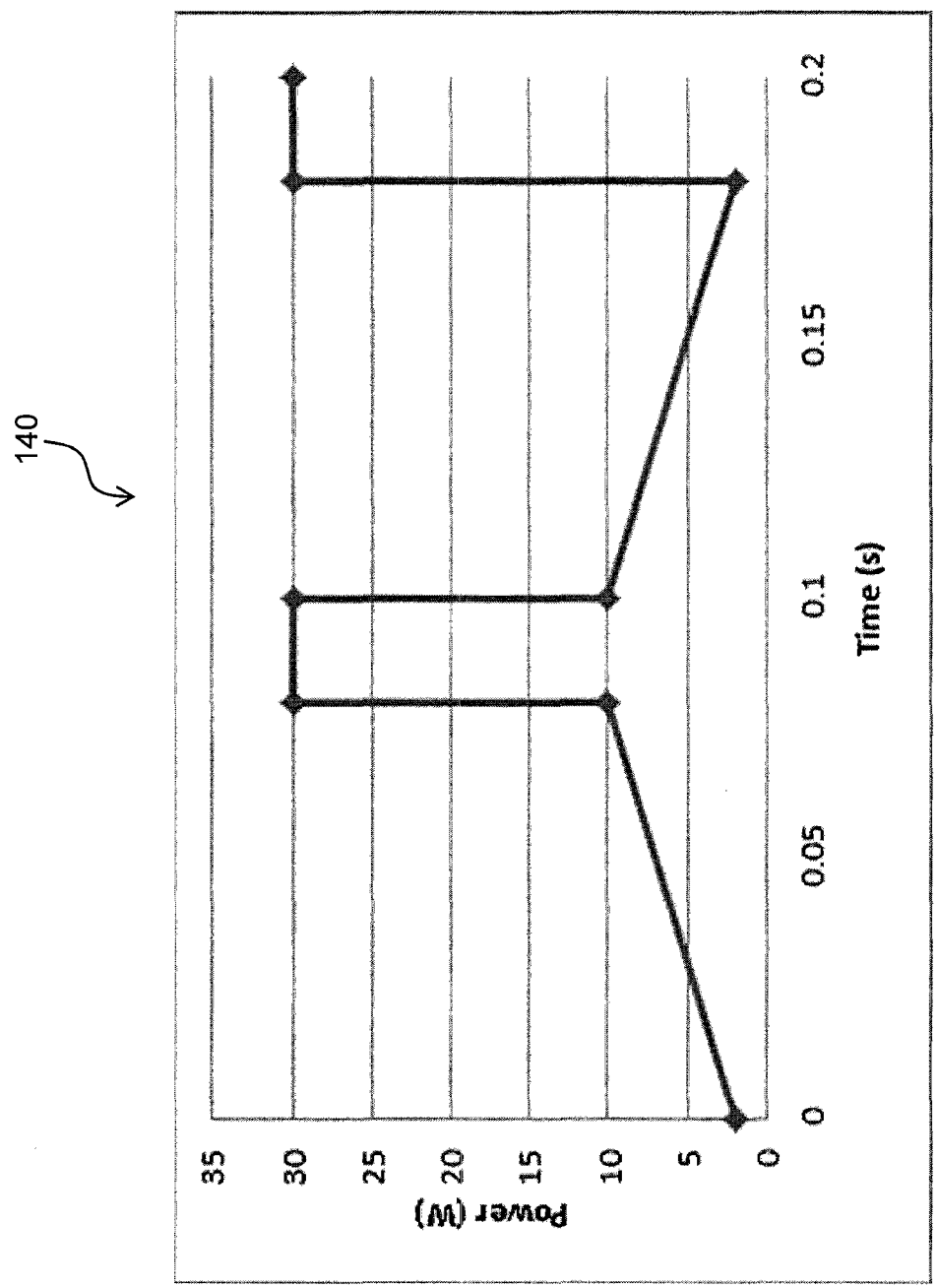
FIG. 11 shows a graphical representation of a group of start/end duration segments to intermittently increase the power delivered to the tip of an electrosurgical instrument according to principles of the present invention.

Turning now to FIG. 11, there is shown a graphical representation of a group of start/end duration segments, generally indicated at 140, to intermittently increase the power delivered to the tip of an electrosurgical instrument according to principles of the present invention. When operating a surgical instrument at lower temperatures, for example, when it is desired to coagulate tissue with minimal collateral thermal damage to surrounding tissue, portions of the tip 60 may tend to stick to the tissue. Under these circumstances, a power control algorithm 140 may be used to intermittently increase the power delivered to the tip 60 so as to substantially prevent the tip 60 from sticking to the tissue being treated. The intermittent power surges may momentarily increase the temperature of the ferromagnetic layer 65 which aids in the prevention of the tip 60 from sticking to the tissue. For example, a power control algorithm may include delivering 5 W or less to the tip 60 for a duration of about 90 ms, increasing the power to about 30 W for 10 ms, decreasing the power to 5 W or less for another 90 ms, increasing the power to about 30 W for 10 ms, etc., until the thermal surgical tool is deactivated. It will be appreciated the powers delivered and the respective duration of their delivery may vary.

According to one aspect of the invention, a thermal surgical instrument may be selectively controlled such that a user may operate the instrument in a mode where power delivery to a surgical tip is managed according to a fixed power index or a mode where power delivery to a surgical tip is managed according to a repeatedly executed power profile. For example power delivery management may be selectively controlled by activating the foot pedals 20 shown in FIG. 1. According to one aspect of the invention, the system may include at least two foot pedals 20 which may be used to by the user to selectively control the mode in which the tip is to be activated. Thus, if the user wants to, for example, incise tissue he or she may activate a first foot pedal 20 to deliver power to the tip according to a fixed power index (e.g. about 5 W to about 60 W). Alternatively, if the user wants to, for example, coagulate tissue he or she may activate a second foot pedal 20 to deliver power to the tip according to a repeatedly executed power profile.

Figure 12:
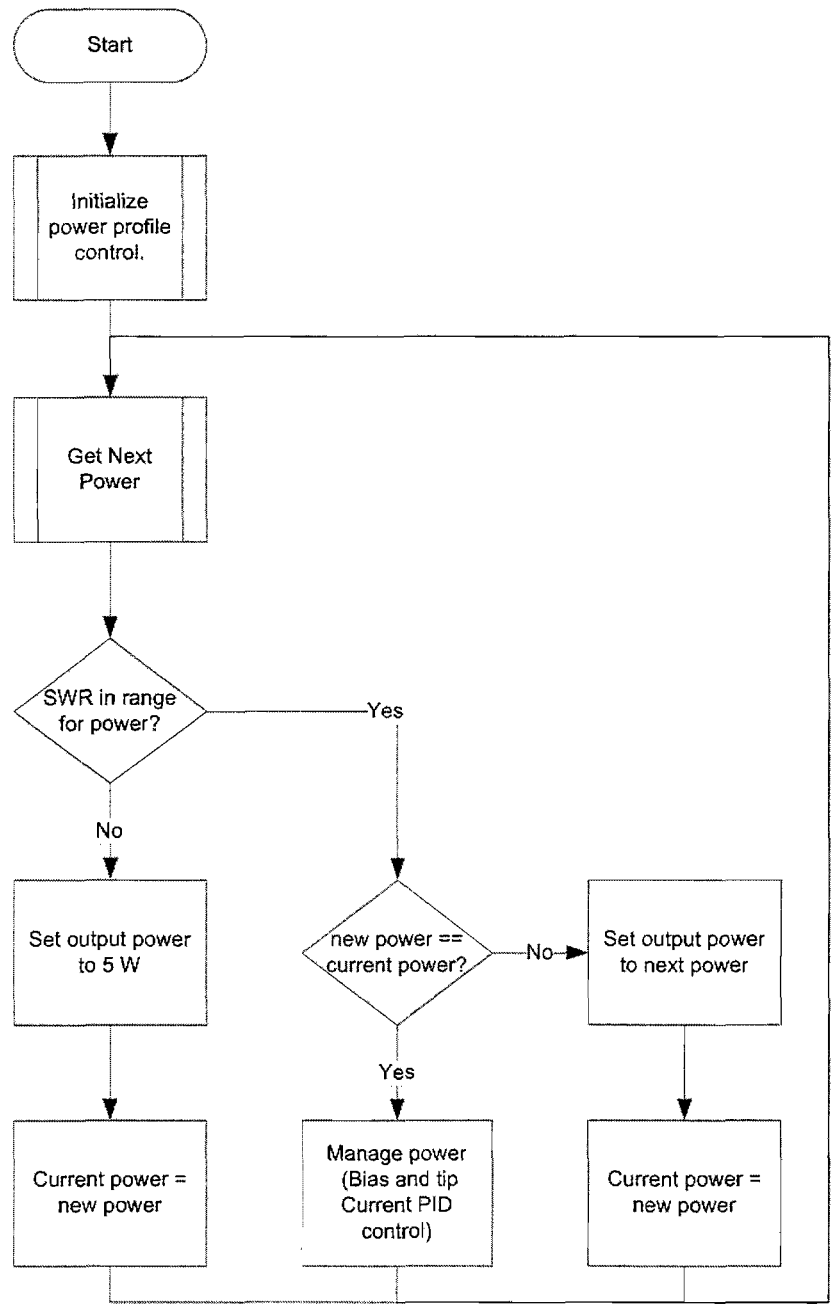
FIG. 12 show a flow chart to illustrate a power profile control algorithm of the present invention.

Turning now to FIG. 12 a flow chart to illustrate a power profile control algorithm of the present invention is shown. In addition to managing power delivery to a surgical tip of thermal surgical element by providing intermittent increases in power, the power profile control algorithm 140 may also manage power delivery to the tip using a state machine similar to that described above.

Figure 13:
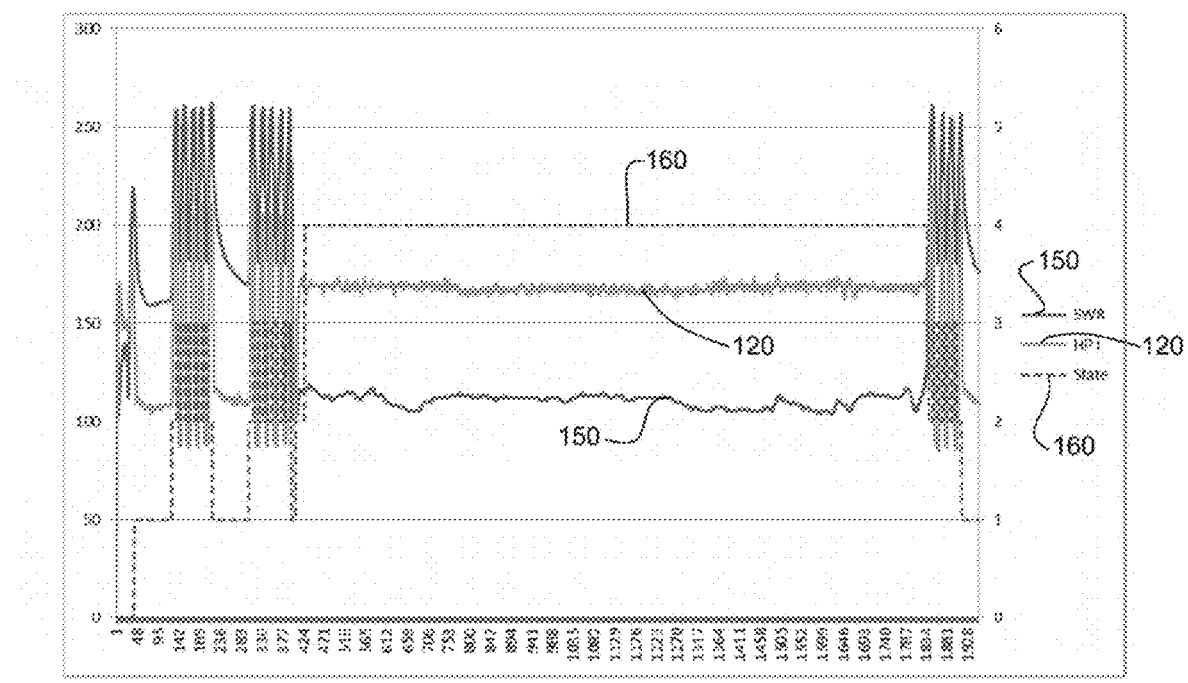
FIG. 13 shows a graphical representation of one example of state management of a thermal surgical instrument according to principles of the present invention.

Turning now to FIG. 13, a graphical representation of one example of state management of a thermal surgical instrument according to principles of the present invention is shown.

Figure 14:
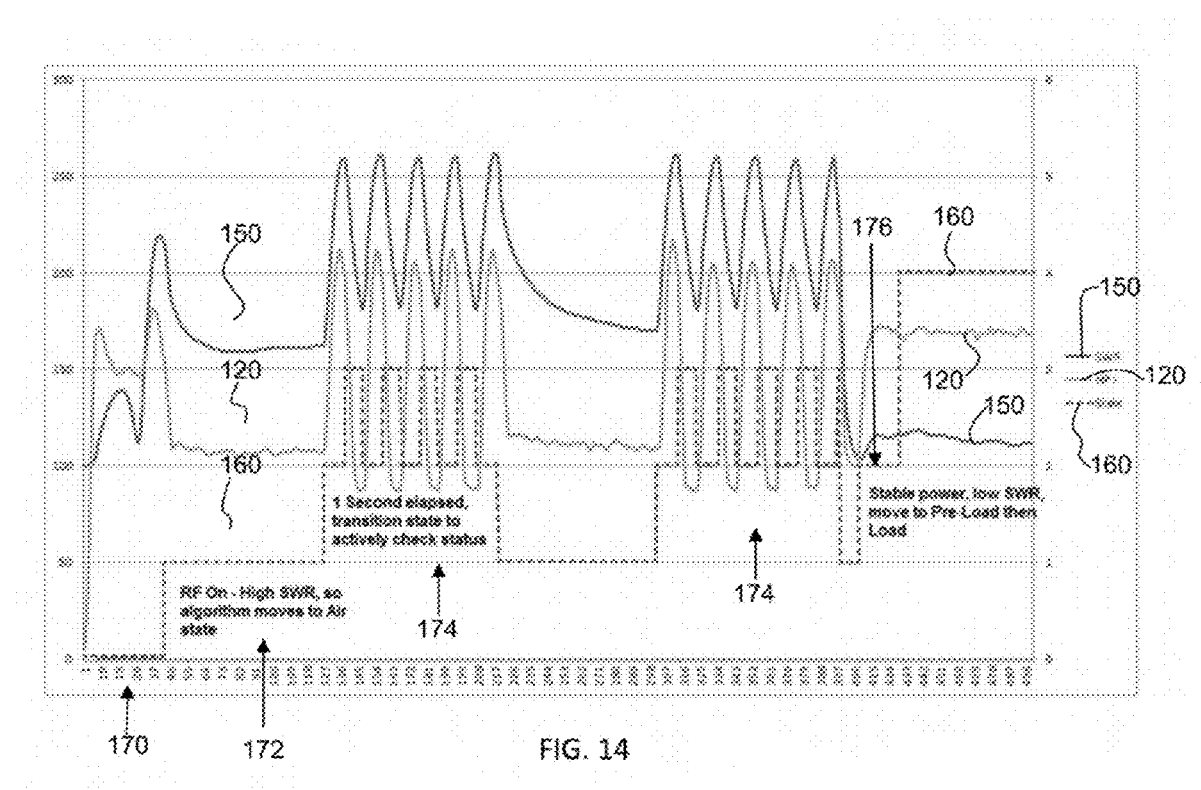
FIG. 14 shows a close-up view of the graphical representation of FIG. 9 upon activation of a tip of the present invention.
Figure 15:
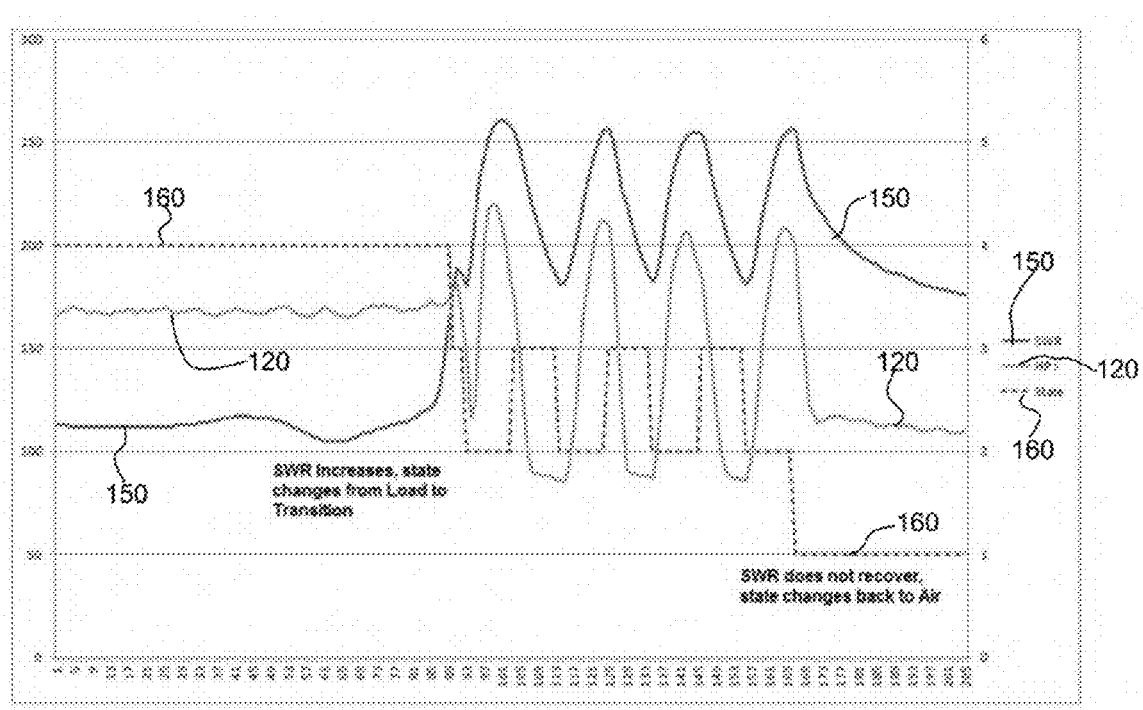
FIG. 15 show a close-up view of the graphical representation of FIG. 9 of the tip transitioning from the Load state back to the Air state.

FIG. 14 shows a close-up view of the graphical representation of FIG. 13 upon activation of a tip of the present invention;

FIG. 15 shows a close-up view of the graphical representation of FIG. 13 of the tip transitioning from the Load state back to the Air state.

Figure 16:
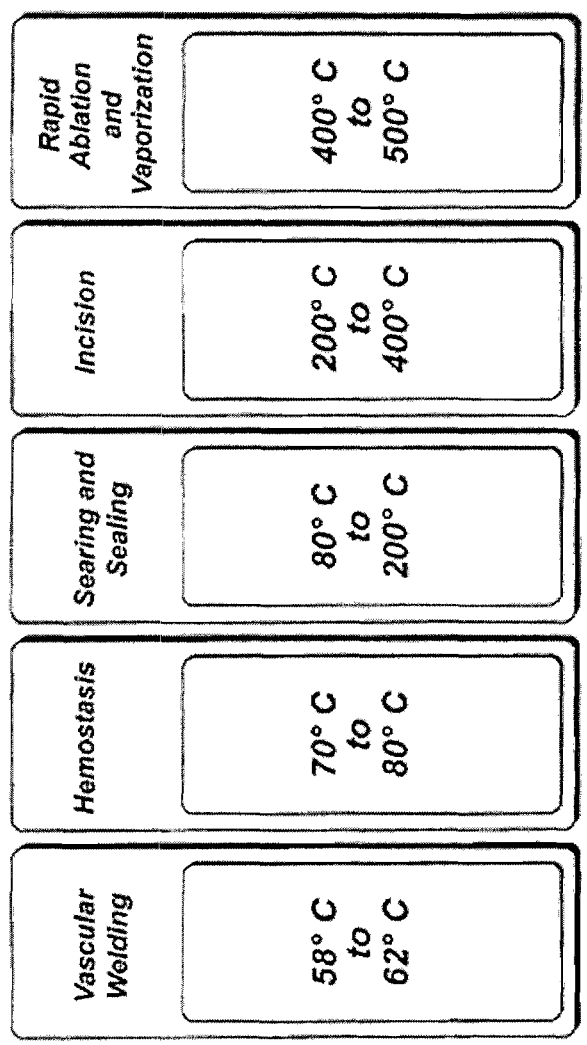
FIG. 16 shows a thermal spectrum as related to tissue effects.

Turning now to FIG. 16, a temperature spectrum is disclosed. Tissue may react differently at different temperatures with a tissue treatment element (such as a ferromagnetic material disposed on a conductor) and thus different treatments for tissue may occur at different temperature ranges. The following temperatures have been found to be useful. Vascular endothelial welding may be optimal at 58-62 degrees Centigrade. Tissue hemostasis without sticking may be achieved at 70-80 degrees Centigrade. At higher temperatures, tissue searing and sealing may occur more quickly, but coagulum may build-up on the instrument. Tissue incision may be achieved at 200 degrees Centigrade with some drag due to tissue adhesion at the edges. Tissue ablation and vaporization may occur rapidly in the 400-500 degree Centigrade range. Although specific tissue treatments may be somewhat variable due to inconsistencies including tissue type and patient differences, to minimize the risk of adverse outcomes to patients, control of the power delivery to a thermal surgical instrument is desirable.

There is thus disclosed an improved electrosurgical and/or thermal surgical instrument and system to control the delivery of power from an energy source to the surgical instrument. It will be appreciated that numerous changes may be made to the present invention without departing from the scope of the claims.

What is claimed is:

1. A method of controlling a thermal cutting or coagulating instrument, comprising:
delivering an oscillating electrical energy to a thermal element, the thermal element comprising a conductor having a ferromagnetic material covering at least a portion of the conductor, the conductor in electrically conductive communication with the ferromagnetic material, and the ferromagnetic material having a thickness being between 0.5 µm and 500 µm;

sensing a behavior characteristic associated with the thermal element; and adjusting delivery of the oscillating electrical energy in response to the behavior characteristic associated with the thermal element.

2. The method according to claim 1, wherein the behavior characteristic associated with the thermal element includes at least one of impedance, current, or standing wave ratio.

3. The method of claim 1, wherein the behavior characteristic is impedance of the thermal element and wherein the method comprises adjusting the delivery of the oscillating electrical energy in response to the impedance of the thermal element to control temperature of the thermal element.

4. The method according to claim 1, wherein the step of delivering the oscillating electrical energy comprises delivering a first oscillating electrical energy; and further comprises the step of sending a pulse of a second oscillating electrical energy to the thermal element, wherein the second oscillating electrical energy is greater in power than the first oscillating electrical energy, and monitoring an effect of the pulse on the behavior characteristic of the thermal element.

5. The method according to claim 1, further comprising the step of intermittently increasing a power of the oscillating electrical energy delivered to the thermal element to periodically increase a temperature of the thermal element.

6. The method according to claim 1, wherein the method comprises storing information relative to a configuration parameter of the thermal element.

7. The method according to claim 6, wherein adjusting the delivery of the oscillating electrical energy further comprises adjusting the delivery of the oscillating electrical energy to control a temperature of the ferromagnetic material.

8. The method according to claim 7, wherein the ferromagnetic material comprises a ferromagnetic sleeve disposed on an insulated conductor.

9. The method according to claim 6, wherein the method further comprises accessing the information relative to the configuration parameter of the thermal element and wherein adjusting the delivery of the oscillating electrical energy further comprises adjusting the delivery of the oscillating electrical energy based on the information.

10. The method of claim 1, wherein the ferromagnetic material has a thickness between 1 µm and 50 µm.

11. A method for regulating a thermal surgical instrument comprising:

selecting a body having a thermal element disposed thereon and disposed in communication with an energy source so as to receive oscillating electrical energy to heat the thermal element, the thermal element comprising a conductor and a layer of ferromagnetic material disposed on the conductor, wherein the layer of ferromagnetic material is in electrically conductive communication with the conductor, the layer of ferromagnetic material having a thickness between 1 µm and 50 µm; and sensing a change in an impedance of the thermal element and generating a signal to adjust the oscillating electrical energy received by the thermal element.

12. The method of claim 11, wherein the method comprises using a power control system having a power control algorithm configured to consistently provide a desired power to the thermal element in response to the signal.

13. The method according to claim 12, wherein the thermal element has a Curie temperature, and wherein the method includes using the power control algorithm to prevent the thermal element of the surgical instrument from exceeding the Curie temperature.

14. The method according to claim 12, wherein the method includes using the power control algorithm to prevent overheating of the thermal surgical instrument at a location other than the thermal element.

15. The method according to claim 12, wherein the method includes using the power control algorithm to control heating of the thermal element to a substantially specific temperature within a range of about plus or minus 30 degrees Centigrade.

16. The method according to claim 12, wherein the power control algorithm is used to regulate a temperature of the ferromagnetic material.

17. The method of claim 11, further comprising using a microcontroller for receiving the signal on a substantially continuous basis.

18. The method of claim 11, wherein the thermal element forms a loop, and wherein the ferromagnetic material covers a portion of the loop.

* * * * *